US011351388B1

(12) United States Patent
O'Driscoll et al.

(10) Patent No.: US 11,351,388 B1
(45) Date of Patent: Jun. 7, 2022

(54) WIRELESS POWER RECEIVER COIL FOR IMPLANTABLE NEUROMODULATION DEVICE

(71) Applicant: Verily Life Sciences LLC, South San Francisco, CA (US)

(72) Inventors: Stephen O'Driscoll, San Francisco, CA (US); Damiano Patron, San Bruno, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 304 days.

(21) Appl. No.: 16/508,628

(22) Filed: Jul. 11, 2019

Related U.S. Application Data

(60) Provisional application No. 62/730,106, filed on Sep. 12, 2018.

(51) Int. Cl.
| | |
|---|---|
| *H02J 7/00* | (2006.01) |
| *A61N 1/378* | (2006.01) |
| *H02J 50/90* | (2016.01) |
| *H02J 50/12* | (2016.01) |

(Continued)

(52) U.S. Cl.
CPC ............ *A61N 1/3787* (2013.01); *H02J 7/025* (2013.01); *H02J 50/12* (2016.02); *H02J 50/70* (2016.02); *H02J 50/90* (2016.02); *A61F 2250/0001* (2013.01)

(58) Field of Classification Search
USPC .................. 320/106, 107, 108, 109, 110, 112
See application file for complete search history.

(56) References Cited

U.S. PATENT DOCUMENTS

| | | | |
|---|---|---|---|
| 6,137,237 | A | 10/2000 | Maclennan et al. |
| 8,847,548 | B2 | 9/2014 | Kesler et al. |
| 8,907,531 | B2 | 12/2014 | Hall et al. |

(Continued)

FOREIGN PATENT DOCUMENTS

| | | | | |
|---|---|---|---|---|
| CN | 207587110 | U | * | 7/2018 |
| EP | 3096337 | A1 | * | 11/2016 ............... H02J 50/40 |

OTHER PUBLICATIONS

U.S. Appl. No. 16/553,866, Non-Final Office Action, dated Mar. 25, 2021, 10 pages.

(Continued)

*Primary Examiner* — Brian Ngo
(74) *Attorney, Agent, or Firm* — Kilpatrick Townsend & Stockton LLP

(57) ABSTRACT

The present disclosure relates to implantable neuromodulation devices, and in particular to a wireless power coil for a neuromodulation device that is to be implanted in a minimally invasive manner, for example, through a trocar or cannula. Particularly, aspects of the present disclosure are directed to a medical device that includes a lossy housing surrounding a power supply, and a receiving coil configured to exchange power wirelessly via a wireless power transfer signal and deliver the power to the power supply. The receiving coil is spaced a predetermined distance from the lossy housing. The medical device further includes a gap provided between the lossy housing and the receiving coil on a vertical plane, and a spacer that fills in at least a portion of the gap to maintain the lossy housing a predetermined distance from the receiving coil.

15 Claims, 12 Drawing Sheets

(51) Int. Cl.
    *H02J 7/02*         (2016.01)
    *H02J 50/70*       (2016.01)

(56) References Cited

U.S. PATENT DOCUMENTS

| | | | | |
|---|---|---|---|---|
| 2005/0075697 | A1* | 4/2005 | Olson | A61N 1/3787 |
| | | | | 607/61 |
| 2008/0294207 | A1* | 11/2008 | Kast | A61N 1/37514 |
| | | | | 607/2 |
| 2011/0193688 | A1 | 8/2011 | Forsell | |
| 2012/0235501 | A1 | 9/2012 | Kesler et al. | |
| 2012/0235634 | A1 | 9/2012 | Hall et al. | |
| 2014/0265621 | A1* | 9/2014 | Wong | H02J 7/025 |
| | | | | 307/104 |
| 2016/0197511 | A1* | 7/2016 | Atasoy | H02J 50/10 |
| | | | | 307/104 |

OTHER PUBLICATIONS

Khan et al., "Wireless Transfer of Powerto Low Power Implanted Biomedical Devices: Coil Design Considerations", IEEE International Instrumentation and Measurement Technology Conference Proceedings, May 13-16, 2012.

Johns et al., "Designing a Qi-compliant receiver coil for wireless power systems, Part 1", Analog Applications Journal, 2012, pp. 8-14.

U.S. Appl. No. 16/553,866, Final Office Action, dated Oct. 6, 2021, 10 pages.

\* cited by examiner

WIRELESS POWER RECEIVER COIL FOR IMPLANTABLE NEUROMODULATION DEVICE

CROSS REFERENCE TO RELATED APPLICATIONS

The present application claims priority and benefit from U.S. Provisional Application No. 62/730,106, filed Sep. 12, 2018, entitled "WIRELESS POWER RECEIVER COIL FOR IMPLANTABLE NEUROMODULATION DEVICE", the entire contents of which are incorporated herein by reference for all purposes.

FIELD OF THE INVENTION

The present disclosure relates to implantable neuromodulation devices, and in particular to a wireless power coil for a neuromodulation device that is to be implanted in a minimally invasive manner, for example, through a trocar or cannula.

BACKGROUND

Normal neural activity is an intricate balance of electrical and chemical signals, which can be disrupted by a variety of insults (genetic, chemical or physical trauma) to the nervous system, causing cognitive, motor and sensory impairments. Similar to the way a cardiac pacemaker or defibrillator corrects heartbeat abnormalities, neuromodulation therapies help to reestablish normal neural balance. In particular instances, neuromodulation therapies utilize medical device technologies to enhance or suppress activity of the nervous system for the treatment of disease. These technologies include implantable as well as non-implantable neuromodulation devices and systems that deliver electrical, chemical or other agents to reversibly modify brain and nerve cell activity. The most common neuromodulation therapy is spinal cord stimulation to treat chronic neuropathic pain. In addition to chronic pain relief, some examples of neuromodulation therapies include deep brain stimulation for essential tremor, Parkinson's disease, dystonia, epilepsy and psychiatric disorders such as depression, obsessive compulsive disorder and Tourette syndrome; sacral nerve stimulation for pelvic disorders and incontinence; vagus nerve stimulation for rheumatoid arthritis; gastric and colonic stimulation for gastrointestinal disorders such as dysmotility or obesity; vagus nerve stimulation for epilepsy, obesity or depression; carotid artery stimulation for hypertension, and spinal cord stimulation for ischemic disorders such as angina and peripheral vascular disease.

Neuromodulation devices and systems tend to have a similar form factor, derived from their predecessors, e.g. the pacemaker or defibrillator. Such neuromodulation devices and systems typically comprise an implant device including a neurostimulator having electronics connected to a lead assembly that delivers electrical pulses to electrodes interfaced with nerves or nerve bundles via an electrode assembly. In order to supply energy to the neurostimulator an energy source such as an electrochemical cell or a battery is typically arranged in the neurostimulator (e.g., within the housing of the neurostimulator). However, electrochemical cells and batteries have a limited life time. After the electrochemical cell or battery has been emptied or discharged, it has to be re-charged or replaced when the energy stored is not sufficient for the physiological treatment. In the case of an implanted device such as a neurostimulator it is for several reasons preferred to recharge an electrochemical cell or battery rather than replacing the cell or battery. One reason is the invasive nature associated with removal and replacement of the energy source and the risk to the patient. Other reasons include that some implanted devices consume a relatively large amount of energy and would then have to have their energy sources replaced relatively often, which can be inconvenient and costly for the patient.

One of the non-invasive methods to recharge the electrochemical cell or battery is through wireless power transfer. This method comprises an external power charger and a power receiver embedded into the implant device. The power receiver is typically made by a coil of wire connected to power management circuitry. However, in the case of implant devices meant for both subcutaneous and deeper point applications, the implant devices are typically characterized by a very low thickness profile and implanted via a minimally invasive manner, for example, through a trocar or cannula. Given the very low thickness profile of the implant devices and the small diameter of the trocar or cannula, the coil is often placed next to other components such as metal enclosures for electronic circuitry, which reduces the wireless power transfer efficiency. Thus, wasting energy, requiring longer charge times and/or more frequent charging sessions. In view of these inefficiencies, it is desirable to develop neuromodulation devices and systems that are capable of having design flexibility, and desirable mechanical properties to increase the wireless power transfer efficiency.

BRIEF SUMMARY

In various embodiments, a medical device is provided that includes: a lossy housing surrounding a power supply; and a receiving coil configured to exchange power wirelessly via a wireless power transfer signal and deliver the power to the power supply. The receiving coil is spaced a predetermined distance from the lossy housing; and the predetermined distance is determined based on: (i) a size constraint of a delivery mechanism for the medical device, (ii) a size of the lossy housing, (iii) an area of the receiving coil, and (iv) a coupling factor between the receiving coil and a transmitting coil of greater than 0.5.

In some embodiments, the delivery mechanism is another medical device comprising a lumen defined by the size constraint, and wherein the medical device has a size configured to fit within the size constraint of the lumen such that the medical device can be implanted in a patient through the delivery mechanism. Optionally, the delivery mechanism is a laparoscopic port.

In some embodiments, the size of the medical device includes a width of less than 24 mm, a height of less than 15 mm, and a length of less than 80 mm. In some embodiments, the size of the lossy housing includes a width of less than 24 mm, a height of less than 10 mm, and a length of less than 80 mm. In some embodiments, the receiving coil has a quality factor of greater than 50. In some embodiments, the receiving coil has a quality factor of greater than 100.

In some embodiments, the receiving coil is comprised gold (Au), gold/chromium (Au/Cr), platinum (Pt), platinum/iridium (Pt/Ir), titanium (Ti), gold/titanium (Au/Ti), or any alloy thereof. In some embodiments, the housing is comprised of metal. Optionally, the metal is titanium or an alloy thereof.

In some embodiments, the predetermined distance is from 250 µm to 20 mm. In some embodiments, the size constraint of the delivery mechanism includes a diameter of less than 30 mm. In some embodiments, the size constraint of the delivery mechanism includes a width of less than 30 mm, a height of less than 30 mm, and a length of less than 250 mm. In some embodiments, the area of the receiving coil is determined based on: (i) the size constraint of the delivery mechanism, (ii) the size of the lossy housing, and (iii) the coupling factor between the receiving conductor structure and the transmitting conductor structure of greater than 0.5.

In some embodiments, the receiving coil has a height that is determined based on: (i) a height or diameter of the size constraint, (ii) a height of the lossy housing, and (iii) the predetermined distance. In some embodiments, the receiving coil has a width that is determined based on: (i) a width or diameter of the size constraint. In some embodiments, the receiving coil has a length that is determined based on: (i) a length of the size constraint. In some embodiments, the area of the receiving coil is determined based on: (i) the height of the receiving coil, (ii) the width of the receiving coil, (iii) the length of the receiving coil, and (iv) the coupling factor between the receiving coil and the transmitting coil of greater than 0.5.

In various embodiments, a medical device is provided that includes a housing; a power supply within the housing and connected to an electronics module; and a receiving coil configured to exchange power wirelessly via a wireless power transfer signal and deliver the power to the power supply. The receiving coil is a helical structure comprising a first turn, a last turn, and one or more turns disposed between the first turn and the last turn; and a width of the first turn is less than a width of the last turn.

In some embodiments, the one or more turns have a sequential increase in width from the first turn to the last turn such that a shape of the receiving coil is a pyramid. In some embodiments, the receiving coil is spaced a predetermined distance from the housing, and wherein the predetermined distance is determined based on: (i) a size constraint of a delivery mechanism for the medical device, (ii) a size of the housing, (iii) an area of the receiving coil, and (iv) a coupling factor between the receiving coil and a transmitting coil of greater than 0.5. Optionally, the delivery mechanism is another medical device comprising a lumen defined by the size constraint, and wherein the medical device has a size configured to fit within the size constraint of the lumen such that the medical device can be implanted in a patient through the delivery mechanism. Optionally, the delivery mechanism is a laparoscopic port.

In some embodiments, the receiving coil has a height that is determined based on: (i) a pitch between each turn of the receiving coil, (ii) a height or diameter of the size constraint, (iii) a height of the housing, and (iv) the predetermined distance. In some embodiments, the receiving coil has a width that is determined based on: (i) a width or diameter of the size constraint. In some embodiments, the receiving coil has a length that is determined based on: (i) a length of the size constraint. In some embodiments, the area of the receiving coil is determined based on: (i) the height of the receiving coil, (ii) the width of the receiving coil, (iii) the length of the receiving coil, and (iv) the coupling factor between the receiving coil and the transmitting coil of greater than 0.5.

In various embodiments, a wireless power transfer system is provided comprising: a transmitting conductive structure configured to exchange power wirelessly via a wireless power transfer signal; and a receiving conductive structure integrated into a lossy environment comprising a lossy component, wherein the receiving conductive structure is configured to exchange power wirelessly with the transmitting conductive structure via the wireless power transfer signal. The receiving conductive structure is spaced a predetermined distance from the lossy component; and the predetermined distance is determined based on: (i) a size constraint of a delivery mechanism for the lossy environment, (ii) a size of the lossy component, (iii) an area of the receiving conductive structure, and (iv) a coupling factor between the receiving conductive structure and a transmitting conductive structure of greater than 0.5.

In some embodiments, the transmitting conductive structure and the receiving conductive structure have a quality factor of greater than 50. In some embodiments, the transmitting conductive structure and the receiving conductive structure have a quality factor of greater than 100.

In some embodiments, the transmitting conductive structure and the receiving conductive structure are comprised of gold (Au), gold/chromium (Au/Cr), platinum (Pt), platinum/iridium (Pt/Ir), titanium (Ti), gold/titanium (Au/Ti), or any alloy thereof. In some embodiments, the lossy component is comprised of metal. Optionally, the metal is titanium or an alloy thereof.

In some embodiments, the predetermined distance is from 250 μm to 20 mm. In some embodiments, the receiving conductive structure is a helical structure comprising a first turn, a last turn, and one or more turns disposed between the first turn and the last turn; and wherein a width of the first turn is less than a width of the last turn. In some embodiments, the area of the receiving conductive structure is determined based on: (i) the size constraint of the delivery mechanism, (ii) the size of the lossy component, and (iii) the coupling factor between the receiving conductor structure and the transmitting conductor structure of greater than 0.5.

In various embodiments, a medical device is provided comprising: a housing; a power supply within the housing and connected to an electronics module; and a receiving coil configured to exchange power wirelessly via a wireless power transfer signal and deliver the power to the power supply. The receiving coil is a two-dimensional or planar structure comprising a one or more conductive traces formed on a substrate; and the two-dimensional or planar structure is rolled up into a three-dimensional structure.

In some embodiments, a size of the three-dimensional structure is determined based on: (i) a size constraint of a delivery mechanism for the medical device, (ii) a size of the housing, (iii) an area of the receiving coil, and (iv) a coupling factor between the receiving coil and a transmitting coil of greater than 0.5. In some embodiments, the one or more conductive traces are formed with a predetermined shape on the substrate. Optionally, the predetermined shape is a spiral.

In some embodiments, the delivery mechanism is another medical device comprising a lumen defined by the size constraint, and wherein the medical device has a size configured to fit within the size constraint of the lumen such that the medical device can be implanted in a patient through the delivery mechanism. Optionally, the delivery mechanism is a laparoscopic port.

In various embodiments, a neuromodulation system is provided including: a transmitting conductive structure configured to exchange power wirelessly via a wireless power transfer signal; and an implantable neurostimulator including: a lossy housing; a connector attached to a hole in the lossy housing; one or more feedthroughs that pass through the connector; an electronics module within the lossy housing and connected to the one or more feedthroughs; a power supply within the lossy housing and connected to the electronics module; and a receiving conductive structure disposed outside of the housing and connected to the power supply. The receiving conductive structure is configured to exchange power wirelessly with the transmitting conductive structure via the wireless power transfer signal and deliver the power to the power supply; the receiving conductive structure is spaced a predetermined distance from the lossy housing; and the predetermined distance is determined based on: (i) a size constraint of a delivery mechanism for the neuromodulation system, (ii) a size of the lossy housing, (iii) an area of the receiving conductive structure, and (iv) a coupling factor between the receiving conductive structure and a transmitting conductive structure of greater than 0.5. The neuromodulation system may further include a lead assembly including: a lead body including a conductor material; a lead connector that connects the conductor material to the one or more feedthroughs; and one or more electrodes connected to the conductor material.

In some embodiments, the size constraint of the implantable neurostimulator includes a width of less than 24 mm, a height of less than 15 mm, and a length of less than 80 mm. In some embodiments, the area of the receiving conductive structure is determined based on: (i) the size constraint of the delivery mechanism, (ii) the size of the lossy component, and (iii) the coupling factor between the receiving conductor structure and the transmitting conductor structure of greater than 0.5.

In some embodiments, the transmitting conductive structure and the receiving conductive structure have a quality factor of greater than 50. In some embodiments, the transmitting conductive structure and the receiving conductive structure have a quality factor of greater than 100.

In some embodiments, the transmitting conductive structure and the receiving conductive structure are comprised of gold (Au), gold/chromium (Au/Cr), platinum (Pt), platinum/iridium (Pt/Ir), titanium (Ti), gold/titanium (Au/Ti), or any alloy thereof. In some embodiments, the lossy housing is comprised of metal. Optionally, the metal is titanium or an alloy thereof. In some embodiments, the predetermined distance is from 250 µm to 20 mm. In some embodiments, the receiving conductive structure is a helical structure comprising a first turn, a last turn, and one or more turns disposed between the first turn and the last turn; and wherein a width of the first turn is less than a width of the last turn.

BRIEF DESCRIPTION OF THE DRAWINGS

The present invention will be better understood in view of the following non-limiting figures, in which:

FIGS. 5A-4E show a wireless power receiver coil with a two-dimensional structure that can be rolled into a three-dimensional structure in accordance with various embodiments.

DETAILED DESCRIPTION

I. Introduction

Figure 1:
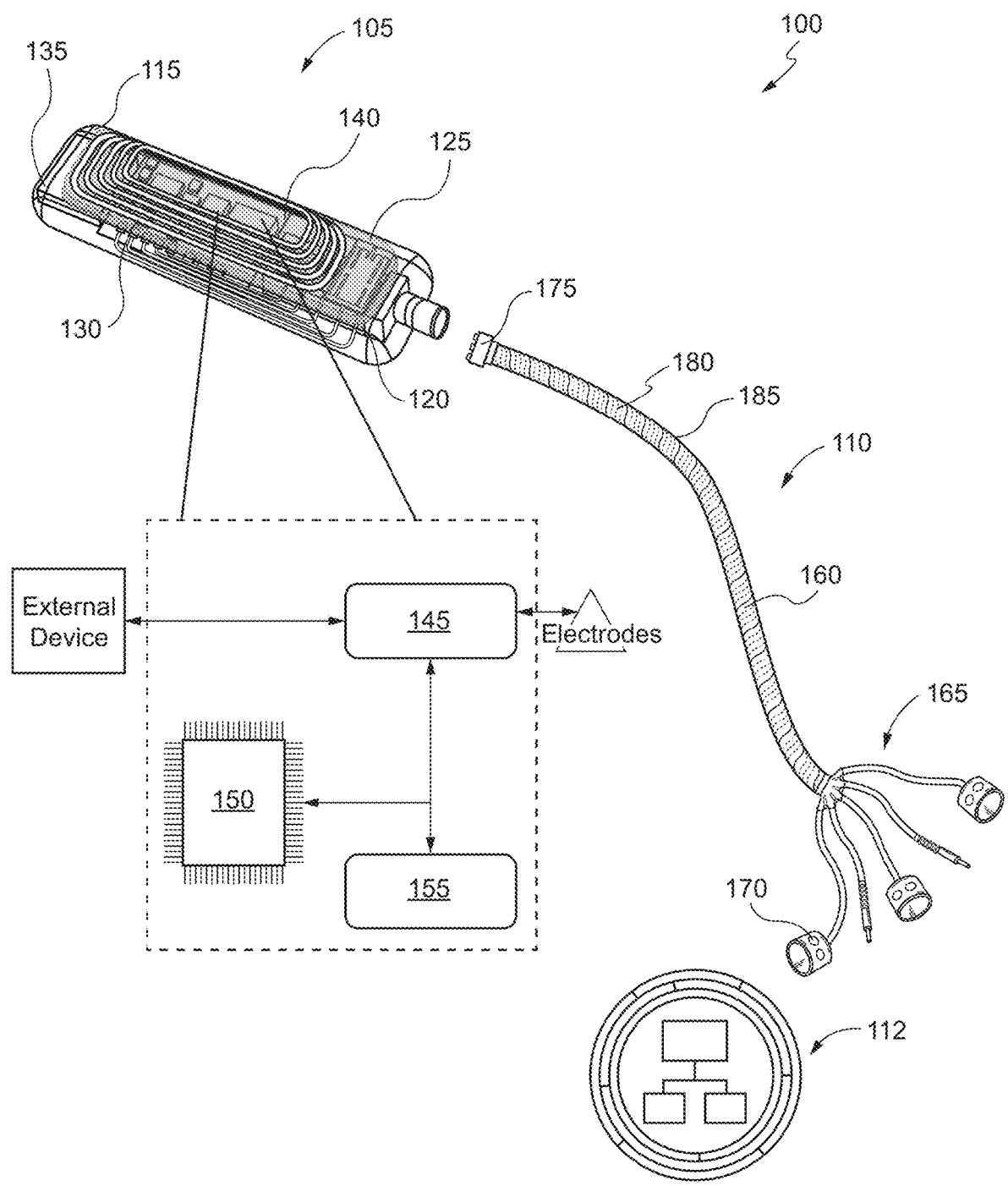
FIG. 1 shows an shows a neuromodulation system in accordance with various embodiments.

The following disclosure describes a wireless power coil for a neuromodulation device that is to be implanted in a minimally invasive manner, for example, through a trocar or cannula. The basic principle of an inductively coupled power transfer system includes a transmitter coil and a receiver coil. Both coils form a system of magnetically coupled inductors. An alternating current in the transmitter coil generates a magnetic field which induces a voltage in the receiver coil. By attaching a load to the receiver coil the voltage can be used to power an electronic device or charge a battery. The magnetic field generated by the transmitter coil radiates (approximately equally) in all directions, hence the flux drops rapidly with distance (obeying an inverse square law). Consequently, the receiver coil must be placed as close as possible to the transmitter coil (less than 10 mm) to intercept the most flux. This requirement of a close proximity between the transmitter coil and the receiver coils is not always practical for neuromodulation therapy, especially instances in which the neurostimulator is implanted deeper than the subcutaneous layer (e.g., within the brain or thoracic cavity).

Alternative, wireless charging systems have been developed that transfer power between a transmitter coil and a receiver coil that are operating at identical resonant frequencies (determined by the coils' distributed capacitance, resistance and inductance). The basic premise is that the energy "tunnels" from one coil to the other instead of radiating in all directions from the primary coil; and thus resonant wireless charging is not governed by the inverse square law. This technique is still "inductive" in that the oscillating magnetic field generated by the transmitter coil induces a current in the receiver coil and takes advantage of the strong coupling that occurs between resonant coils even when separated by tens of centimeters. Resonant wireless charging addresses the main drawbacks of inductive wireless charging, which is the requirement to closely couple the coils and the demand for precise alignment from the user. However, resonant wireless charging is not without its own drawbacks. A primary drawback is a relatively low efficiency due to flux leakage (even at close range a well-designed system might demonstrate an efficiency of 30% at 2 cm, dropping to 15% at 75 cm coil separation, greater circuit complexity and, because of the (typically) high operating frequencies, potential electromagnetic interference (EMI) challenges.

The efficiency of the power transfer in resonant wireless charging depends on the energy coupling rate between the coils and the characteristic parameters for each coil (i.e., inductor). The amount of inductive coupling between coils is measured by their mutual inductance. The strength of the coupling may be expressed as a coupling factor, which is determined by the area of the coils including the distance between the coils, the ratio of width of the receiver coil/width of the transmitter coil, the shape of the coils and the angle between the coils. The characteristic parameters for each coil includes the resonance frequency and the intrinsic loss rate of the coils. A quality factor measures how well the system stores energy and is expressed as the ratio of the resonance frequency matching between the coils and the intrinsic loss rate of the coils. A higher quality factor indicates a lower rate of energy loss relative to the stored energy of the coils; the oscillations die out more slowly. Resonance allows the wireless power transfer system to operate at greater distances compared to a non-resonant one. However, frequency mismatch may be observed, which has the effect of limiting the maximum power stored and thus transferred. One factor that may influence the coupling factor and the quality factor of the coils is the external environment near the coils. In particular, the close proximity of an environmental factor such as metal or tissue has been found to greatly influence the efficiency of the wireless power transfer system.

Most conventional wireless power transfer systems involve transferring power between a transmitting coil and a receiving coil in free space without nearby environmental factors. Consequently, the best possible efficiency of most conventional wireless power transmission systems depends on the coupling factor between the coils and the quality factors. However, for a low profile implanted device meant for subcutaneous and deeper applications and implanted via a minimally invasive manner, for example, through a trocar or cannula, the various components of the neurostimulator are packed into a tight volume of space. In a low profile implanted device, this means that the receiving coil will likely be placed next to a number of environmental factors including the metal enclosure, which has been found to influence the coupling (e.g., reduce the energy available to the receiving coil due to energy absorption and change of field shape) and the quality factor of the coils (e.g., create a frequency mismatch).

To address these limitations and problems, it has been discovered that to improve efficiency of the wireless power transfer in a system with environmental factors it is important to maintain sufficient spacing between the coils and the environmental factors. Given a fixed area or volume for the delivery mechanism (e.g., trocar or cannula) of the implantable device and wireless power transfer coil, maximizing the coil area to maintain sufficient coupling and keeping enough spacing to avoid the influence from the environmental factors means that it is important to find a tradeoff between these requirements. One illustrative embodiment of the present disclosure is directed to a medical device that comprises a lossy housing surrounding a power supply; and a receiving coil configured to exchange power wirelessly via a wireless power transfer signal and deliver the power to the power supply. The receiving coil is spaced a predetermined distance from the lossy housing. The predetermined distance is determined based on: (i) a size constraint of a delivery mechanism for the medical device, (ii) a size of the lossy housing, (iii) an area of the receiving coil, and (iv) a coupling factor between the receiving coil and a transmitting coil of greater than 0.5.

In other embodiments, a medical device is provided comprising: a housing; power supply within the housing and connected to an electronics module; and a receiving coil configured to exchange power wirelessly via a wireless power transfer signal and deliver the power to the power supply. The receiving coil is a helical structure comprising a first turn, a last turn, and one or more turns disposed between the first turn and the last turn. A width of the first turn is less than a width of the last turn. The one or more turns may have a sequential increase in width from the first turn to the last turn such that a shape of the receiving coil is a pyramid.

In other embodiments, a wireless power transfer system is provided comprising a transmitting conductive structure configured to exchange power wirelessly via a wireless power transfer signal; and a receiving conductive structure integrated into a lossy environment comprising a lossy component. The receiving conductive structure is configured to exchange power wirelessly with the transmitting conductive structure via the wireless power transfer signal. The receiving conductive structure is spaced a predetermined distance from the lossy component. The predetermined distance is determined based on: (i) a size constraint of a delivery mechanism for the lossy environment, (ii) a size of the lossy component, (iii) an area of the receiving conductive structure, and (iv) a coupling factor between the receiving conductive structure and a transmitting conductive structure of greater than 0.5.

In other embodiments, a medical device is provided comprising: a housing; power supply within the housing and connected to an electronics module; and a receiving coil configured to exchange power wirelessly via a wireless power transfer signal and deliver the power to the power supply. The receiving coil is a two-dimensional or planar structure comprising a one or more conductive traces formed on a substrate. The two-dimensional or planar structure is rolled up into a three-dimensional structure.

In other embodiments, a neuromodulation system is provided comprising a transmitting conductive structure configured to exchange power wirelessly via a wireless power transfer signal; an implantable neurostimulator including: a lossy housing; a connector attached to a hole in the lossy housing; one or more feedthroughs that pass through the connector; an electronics module within the lossy housing and connected to the one or more feedthroughs; a power supply within the lossy housing and connected to the electronics module; and a receiving conductive structure disposed outside of the housing and connected to the power supply. The receiving conductive structure is configured to exchange power wirelessly with the transmitting conductive structure via the wireless power transfer signal and deliver the power to the power supply. The receiving conductive structure is spaced a predetermined distance from the lossy housing, and the predetermined distance is determined based on: (i) a size constraint of a delivery mechanism for the neuromodulation system, (ii) a size of the lossy housing, (iii) an area of the receiving conductive structure, and (iv) a coupling factor between the receiving conductive structure and a transmitting conductive structure of greater than 0.5. The neuromodulation system further comprises a lead assembly including: a lead body including a conductor material; a lead connector that connects the conductor material to the one or more feedthroughs; and one or more electrodes connected to the conductor material.

Advantageously, these approaches provide a neuromodulation system, which has a very low thickness profile that is capable of being implanted in a minimally invasive manor, an efficient wireless power transfer, and greater design flexibility. More specifically, these approaches enable for spacing between the wireless power receiving coil and environmental factors presented by the neuromodulation system while also maximizing the area of the wireless power receiving coil in order to maximize the wireless power transfer into the implanted neurostimulator.

II. Neuromodulation Devices and Systems with Wireless Power Transfer

FIG. 1 shows a neuromodulation system 100 in accordance with some aspects of the present invention. In various embodiments, the neuromodulation system 100 includes an implantable neurostimulator 105, a lead assembly 110, and a transmitting conductive structure 112 (e.g., a transmitting coil). The implantable neurostimulator 105 may include a housing 115, a connector 120, a power source 125, a receiving conductive structure 130 (e.g., a wireless power coil or a receiving coil), an antenna 135, and an electronics module 140 (e.g., a computing system). The housing 115 may be comprised of materials that are biocompatible such as bioceramics or bioglasses for radio frequency transparency, or metals such as titanium or alloys thereof. In accordance with various aspects, the size and shape of the housing 115 is selected such that the neurostimulator 105 can be implanted within a patient. In the example shown in FIG. 1, the connector 120 is attached to a hole in a surface of the housing 115 such that the housing 115 is hermetically sealed. The connector 120 may include one or more feedthroughs (i.e., electrically conductive elements, pins, wires, tabs, pads, etc.) mounted within a header and extending through the surface of the header from an interior to an exterior of the header. The power source 125 (e.g., a battery) may be within the housing 115 and connected (e.g., electrically connected) to the electronics module 140 to power and operate the components of the electronics module 140. In some embodiments, the power source 125 and the electronics module 140 are surrounded by the housing 115. The wireless power coil 130 may be outside the housing 115 and configured to receive electrical energy from the charging device 112. In some embodiments, the wireless power coil 130 is attached to an outside surface of the housing 115 by a spacer 142. The wireless power coil 130 is connected (e.g., electrically connected) to the power source 125 to provide the electrical energy to recharge or supply power to the power source 125. The antenna 135 may be outside the housing 115 and connected (e.g., electrically connected) to the electronics module 140 for wireless communication with external devices via, for example, radiofrequency (RF) telemetry.

In some embodiments, the electronics module 140 may be connected (e.g., electrically connected) to interior ends of the connector 120 such that the electronics module 140 is able to apply a signal or electrical current to conductive traces of the lead assembly 110 connected to exterior ends of the connector 120. The electronics module 140 may include discrete and/or integrated electronic circuit components that implement analog and/or digital circuits capable of producing the functions attributed to the neuromodulation devices or systems such as applying or delivering neural stimulation to a patient. In various embodiments, the electronics module 140 may include software and/or electronic circuit components such as a pulse generator 145 that generates a signal to deliver a voltage, current, optical, or ultrasonic stimulation to a nerve or artery/nerve plexus via electrodes, a controller 150 that determines or senses electrical activity and physiological responses via the electrodes and sensors, controls stimulation parameters of the pulse generator 145 (e.g., control stimulation parameters based on feedback from the physiological responses), and/or causes delivery of the stimulation via the pulse generator 145 and electrodes, and a memory 155 with program instructions operable on by the pulse generator 145 and the controller 150 to perform one or more processes for applying or delivering neural stimulation.

In various embodiments, the lead assembly 110 is a monolithic structure that includes a cable or lead body 160. In some embodiments, the lead assembly 110 further includes one or more electrode assemblies 165 having one or more electrodes 170, and optionally one or more sensors. In some embodiments, the lead assembly 110 further includes a lead connector 175. In certain embodiments, the lead connector 175 is bonding material that bonds conductor material of the lead body 160 to the electronics module 140 of the implantable neurostimulator 105 via the connector 120. The bonding material may be a conductive epoxy or a metallic solder or weld such as platinum. In other embodiments, the lead connector 175 is conductive wire, conductive traces, or bond pads (e.g., a wire, trace, or bond pads formed of a conductive material such as copper, silver, or gold) formed on a substrate and bonds a conductor of the lead body 160 to the electronics module 140 of the implantable neurostimulator 105. In alternative embodiments, the implantable neurostimulator 105 and the lead body 160 are designed to connect with one another via a mechanical connector 175 such as a pin and sleeve connector, snap and lock connector, flexible printed circuit connectors, or other means known to those of ordinary skill in the art.

The conductor material of the lead body 160 may be one or more conductive traces 180 formed on a supporting structure 185. The one or more conductive traces 180 allow for electrical coupling of the electronics module 140 to the electrodes 170 and/or sensors of the electrode assemblies 165. The supporting structure 185 may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces 180 may be any suitable conductor such as stainless steel, silver, copper or other conductive materials, which may have separate coatings or sheathing for anticorrosive, insulative and/or protective reasons.

The electrode assemblies 165 may include the electrodes 170 and/or sensors fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 165 include a base material that provides support for microelectronic structures including the electrodes 170, a wiring layer, optional contacts, etc. In some embodiments, the base material is the supporting structure 185. The wiring layer may be embedded within or located on a surface of the supporting structure 185. The wiring layer may be used to electrically connect the electrodes 170 with the one or more conductive traces 180 directly or indirectly via a lead conductor. The term "directly", as used herein, may be defined as being without something in between. The term "indirectly", as used herein, may be defined as having something in between. In some embodiments, the electrodes 170 may make electrical contact with the wiring layer by using the contacts.

III. Wireless Power Transfer System

Figure 2:
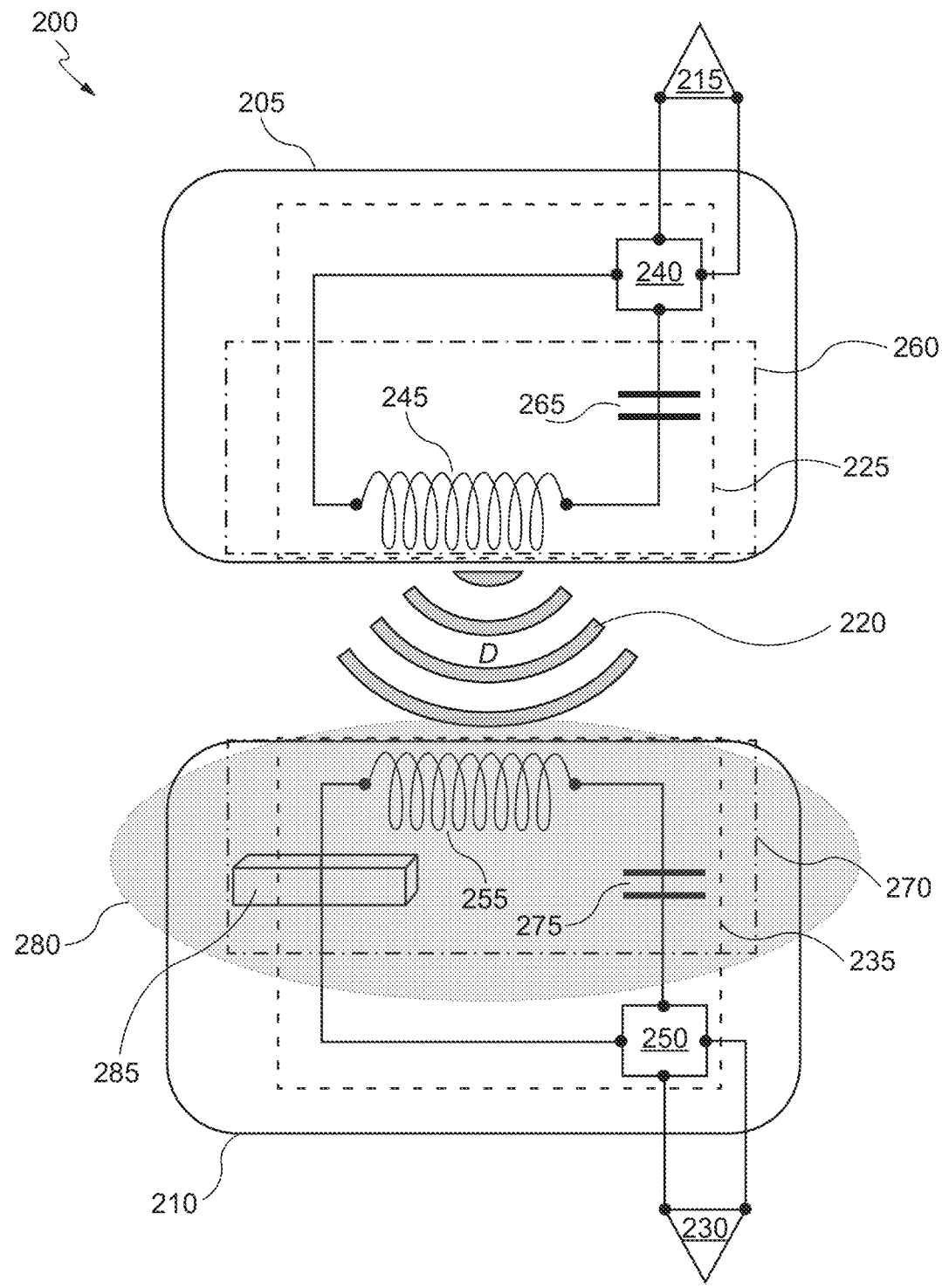
FIG. 2 shows a wireless power transfer system in accordance with various embodiments.

FIG. 2 shows a wireless power transfer system 200 comprising a transmitting device 205 and a receiving device 210 spaced apart from one another by a distance (D). In some embodiments, the transmitting device 205 is connected to a power supply 215 such a main power line. The transmitting device 205 is configured to convert input power (DC or AC electric current) from the power supply 215 into a wireless power transfer signal 220. For example, the input power is converted into the wireless power transfer signal 220 by a first coupling device 225. In some embodiments, the wireless power transfer signal 220 is a time varying electromagnetic field. The receiving device 210 is configured to receive the wireless power transfer signal 220, convert the wireless power transfer signal 220 into an output power (AC or DC electric current), and deliver the output power to a load 230 (e.g., the power source 125 described with respect to FIG. 1). For example, the wireless power transfer signal 220 is converted into the output power by a second coupling device 235. Accordingly, the second coupling device 235 is configured to exchange power wirelessly with the first coupling device 225 via the wireless power transfer signal 220.

In some embodiments, the first coupling device 225 includes an optional oscillator 240 and a transmitting conductive structure 245 (e.g., a transmitting conductive structure 112 described with respect to FIG. 1). In some embodiments, the transmitting conductive structure 245 is a transfer coil of wire configured to exchange power wirelessly via the wireless power transfer signal 220. The oscillator 240 may be used to generate a high frequency AC current, which drives the transmitting conductive structure 245 to generate the wireless power transfer signal 220 such as the time varying or oscillating electromagnetic field. In some embodiments, the second coupling device 235 includes an optional rectifier 250 and a receiving conductive structure 255 (e.g., a receiving conductive structure 130 described with respect to FIG. 1). In some embodiments, the receiving conductive structure 255 is a receiving coil of wire configured to exchange power wirelessly with the transmitting conductive structure 245 via the wireless power transfer signal 220. The rectifier 250 may be used to convert the AC current induced at the receiving conductive structure 255 into DC current, which is delivered to the load 235. In some embodiments, the transmitting conductive structure 245 and the receiving conductive structure 255 have a quality factor of greater than 50. In other embodiments, the transmitting conductive structure 245 and the receiving conductive structure 255 have a quality factor of greater than 100.

In some embodiments, the first coupling device 225 further includes a resonant circuit 260 which includes: (i) the transmitting conductive structure 245 connected to a capacitor 265, (ii) the transmitting conductive structure 245 being a self-resonant coil; or (iii) another resonator (not shown) with internal capacitance. In some embodiments, the second coupling device 235 further includes a resonant circuit 270 which includes: (i) the receiving conductive structure 255 connected to a capacitor 275, (ii) the receiving conductive structure 255 being a self-resonant coil; or (iii) another resonator (not shown) with internal capacitance. The first coupling device 225 and the second coupling device 235 are tuned to resonate at a same resonant frequency. The resonance between the transmitting conductive structure 245 and the receiving conductive structure 255 may increase coupling and more efficient power transfer.

In various embodiments, the receiving conductive structure 255 is in a lossy environment 280. As used herein "lossy" means having or involving the dissipation of electrical or electromagnetic energy. In some embodiments, the lossy environment 280 includes one or more lossy environmental factors or components 285, which result in current loss during the wireless power transfer between the transmitting conductive structure 245 and the receiving conductive structure 255. In some embodiments, the lossy environment 280 is an implantable medical device such as a neurostimulator as described with respect to FIG. 1. In some embodiments, the one or more lossy environmental factors or components 285 include body fluid, body tissue, a lossy component of the implantable medical device, or a combination thereof. In certain embodiments, the lossy component of the medical device is a housing comprised of metal. In some embodiments, the metal is titanium or an alloy thereof.

IV. Wireless Power Coil

Figure 3A:
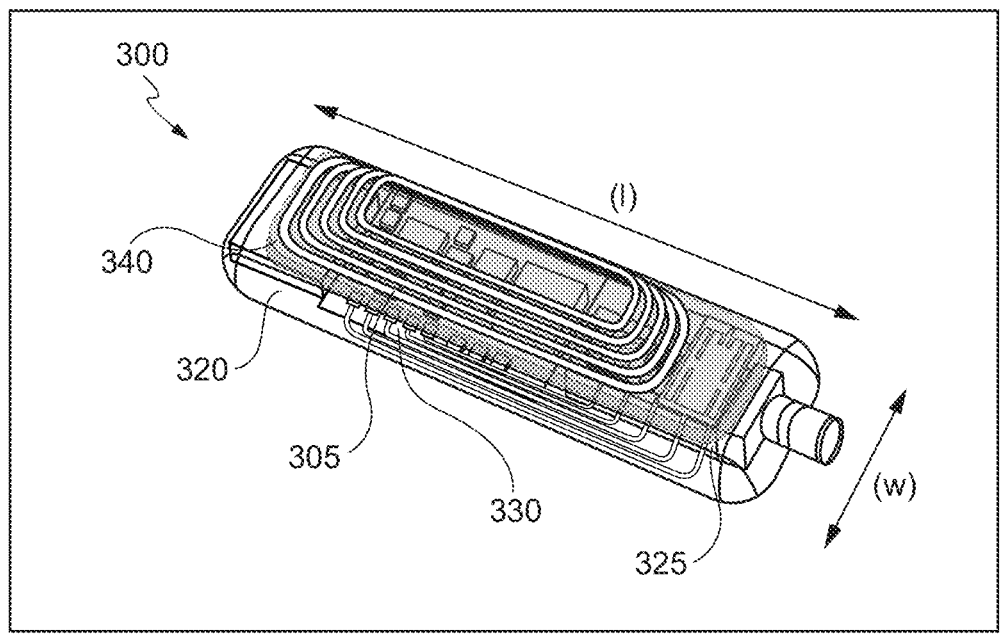
FIGS. 3A-3F show a neurostimulator with a wireless power receiver coil in accordance with various embodiments.
Figure 3B:
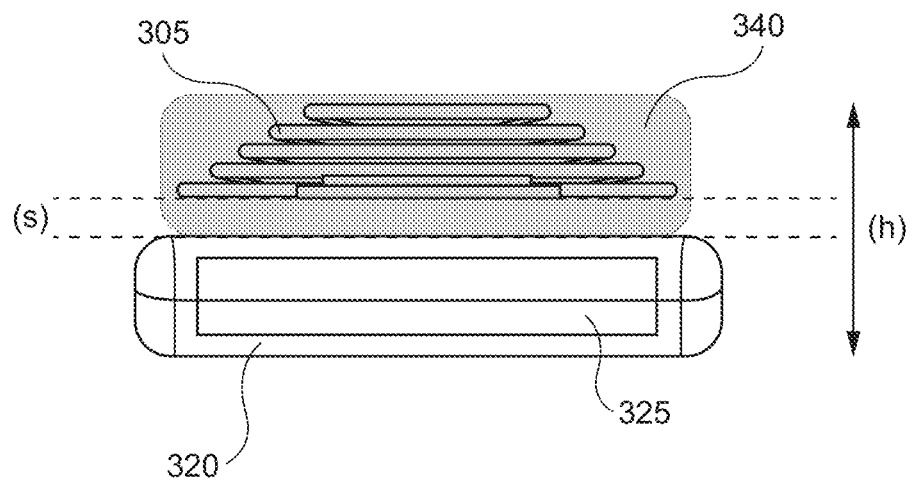
Figure 3C:
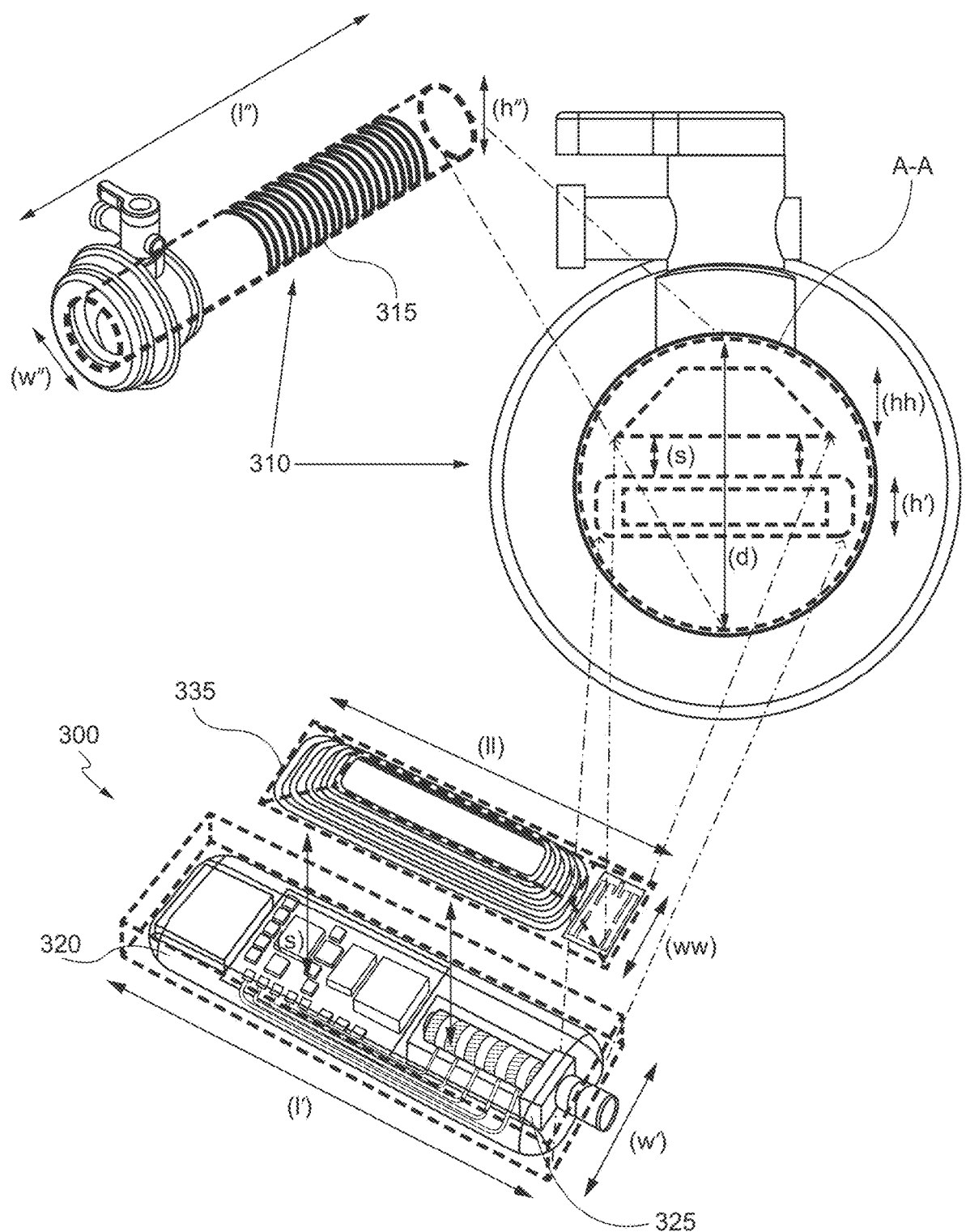

FIGS. 3A, 3B, and 3C show an implantable device 300 (e.g., the implantable neurostimulator 105 described with respect to FIG. 1) comprising a receiving conductive structure 305 (e.g., the receiving conductive structure 255 described with respect to FIG. 2) in accordance with aspects of the present disclosure. In various embodiments, a size of the implantable device 300 is constrained small enough such that the device can be implanted in a less complex and minimally invasive manner, for example, through a delivery mechanism 310. In some embodiments, the delivery mechanism 310 is another medical device (a medical device different from the implantable device 300) comprising a lumen defined by a size constraint 315. The implantable device 300 may be implanted in a patient through the lumen of the delivery mechanism 310. In some embodiments, the implantable device 300 has a size including: (i) a width (w) of less than 24 mm, for example from 10 mm to 20 mm, (ii) a height (h) of less than 15 mm, for example from 5 mm to 13 mm, and (iii) a length (l) of less than 80 mm, for example from 20 mm to 40 mm.

In various embodiments, the receiving conductive structure 305 is physically configured to exchange power wirelessly via a wireless power transfer signal and deliver the power to the power supply. Physically configured means the receiving conductive structure 305 includes: (i) inductance and power receiving capability to meet the needs of the implantable device 300 including the ability to transfer power to the power source with at least an 8% overall efficiency; (ii) the mechanical dimensions (e.g., the height, width and length of the receiving conductive structure 305) fit to the size constraint 315 of the delivery mechanism 310 for the implantable device 300; (iii) the receiving conductive structure 305 is spaced apart from environmental factors to sufficiently avoid coupling of power to the environmental factors; and (iv) the receiving conductive structure 305 is biocompatible and a durable construction for the implanted environment.

In some embodiments, the receiving conductive structure 305 is a receiving coil comprising wound wire. In certain embodiments, the wire is formed from a conductive material. The conductive material may be comprised of various metals or alloys thereof, for example, gold (Au), gold/chromium (Au/Cr), platinum (Pt), platinum/iridium (Pt/Ir), titanium (Ti), gold/titanium (Au/Ti), or any alloy thereof. In some embodiments, the coil has an inductance ranging from 0.5 uH to 50 uH or from 1 uH to 15 uH, for example about 1.2 uH. In some embodiments, the coil has a working frequency ranging from 1 mHz to 100 mHz or from 3 mHz to 50 mHz, for example about 27.12 mHz (ISM Standard Frequency). In some embodiments, the coil has a working voltage ranging from 5 V to 50 V or from 10 V to 35 V, for example about 25 V. In some embodiments, the wire of the coil has an American Wire Gauge (AWG) ranging from 25 AWG to 40 AWG or from 28 AWG to 37 AWG, for example 32 AWG. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

FIGS. 3A, 3B, and 3C show the implantable device 300 may further comprise a lossy housing 320 and optionally a connector 325 attached to an electronics module through a hole 330 in the lossy housing 320 (e.g., the housing 115 and connector 120 described with respect to FIG. 1). In various embodiments, an epoxy covers at least a portion of the implantable device 300 in order to hold the components together and protect the components from environmental factors such as biological fluid. The epoxy may be a resin comprising one or more low molecular weight pre-polymers, one or more higher molecular weight polymers, or combinations thereof, which comprise at least two epoxide groups. In some embodiments, the epoxy covers substantially, if not entirely, the entire device 300 (e.g., the receiving conductive structure 305, the lossy housing 320, the connector 325, and hole 330 are covered). In other embodiments, the epoxy covers select components of the device 300 but not all of the components (e.g., at least the receiving conductive structure 305, the connector 325, and the hole 330 are covered while the lossy housing is exposed). In some embodiments, the lossy housing 320 is comprised of materials that are biocompatible such as bioceramics or bioglasses for radio frequency transparency, or metals such as titanium or an alloy thereof. In some embodiments, the lossy housing 320 has a size including: (i) a width (w') of less than 24 mm, for example from 10 mm to 20 mm, (ii) a height (h') of less than 10 mm, for example from 5 mm to 9 mm, and (iii) a length (l') of less than 80 mm, for example from 20 mm to 40 mm.

As described herein, the lossy housing 320 may be an environmental factor that may influence performance of the receiving conductive structure 305 and thus the performance of the wireless power transfer system. In order to minimize the influence of the lossy housing 320 on the performance of the receiving conductive structure 305, the receiving conductive structure 305 is spaced a predetermined distance (s) from the lossy housing 320. However, the predetermined distance (s) is not boundless as in free space, and instead the predetermined distance (s) is bounded by one or more factors including the size of the implantable device 300, the size of the lossy housing 320, the size constraint 310 of the delivery mechanism 315, an area 335 of the receiving conductive structure 305, a requirement to minimize coupling of power from the receiving conductive structure 305 to the lossy housing 320, and a requirement to limit a shift in the resonance frequency or decrease in the quality factor of the receiving conductive structure 305.

In some embodiments, the predetermined distance (s) is determined based on: (i) the size constraint 315 of the delivery mechanism 310 for the implantable device 300, (ii) the size of the lossy housing 320, (iii) the area 335 of the receiving conductive structure 305, and (iv) a coupling factor between the receiving conductive structure 305 and the transmitting conductive structure of greater than 0.5. In some embodiments, the predetermined distance (s) is less than or equal to 5 mm, from 250 µm to 5 mm, from 250 µm to 20 mm, or from 500 µm to 15 mm, for example about 8 mm. As used herein, when an action or element is "triggered by" or "based on" something, this means the action or element is triggered or based at least in part on at least a part of the something. In some embodiments, the predetermined distance (s) provides a gap between the lossy housing 320 and the receiving conductive structure 305 on a vertical plane. In some embodiments, the predetermined distance (s) or gap between the receiving conductive structure 305 and the lossy housing 320 is maintained with a spacer or covering 340 that is comprised of a medical grade polymer material. In certain embodiments, the spacer or covering 340 fills in at least a portion of the gap to maintain the lossy housing 320 the predetermined distance (s) from the receiving conductive structure 305. In some embodiments, the spacer or covering 340 surrounds the receiving conductive structure 305 and fills in at least a portion of the gap created by the predetermined distance (s) between the receiving conductive structure 305 and the lossy housing 320. In other embodiments, the spacer or covering 340 is attached to one or more surfaces of the receiving conductive structure 305 and fills in at least a portion of the gap created by the predetermined distance (s) between the receiving conductive structure 305 and the lossy housing 320. The medical grade polymer may be thermosetting or thermoplastic. For example, the medical grade polymer may be a soft polymer such as silicone, a polymer dispersion such as latex, a chemical vapor deposited poly(p-xylylene) polymer such as parylene, or a polyurethane such as Bionate® Thermoplastic Polycarbonate-urethane (PCU) or CarboSil® Thermoplastic Silicone-Polycarbonate-urethane (TSPCU).

FIG. 3C shows that determining the predetermined distance (s) involves a tradeoff between increasing the predetermined distance (s), which minimizes coupling of power from the receiving conductive structure 305 to the lossy housing 320, while maintaining a sufficient area 335 for the receiving conductive structure 305 in the size constraint 310 of the delivery mechanism 315 to ultimately achieve a coupling factor between the receiving conductive structure 305 and the transmitting conductive structure of greater than 0.5. The coupling factor is generally determined by the distance (D) between the receiving conductive structure 305 and the transmitting conductive structure and the area encompassed by the receiving conductive structure 305 and the transmitting conductive structure. For example, the greater the amount of the wireless power transfer signal (e.g., the greater the amount of flux from the magnetic field) that reaches the receiving conductive structure 305, the better the conductive structures are coupled and the higher the coupling factor. The amount of the wireless power transfer signal that reaches the receiving conductor structure 305 may be increased by increasing the area 335 of the receiving conductor structure 305. However, the coupling factor may be decreased by the presence of an environmental factor such as the housing 320, which may couple with the receiving conductive structure 305 and leach power that is being transferred to the receiving conductive structure 305.

As shown in FIG. 3C, the implantable device 300 has a size configured to fit within the size constraint 315 of the delivery mechanism 310. In some embodiments, the size of the implantable device 300 includes: (i) a width (w) of less than 24 mm, for example from 5 mm to 15 mm or about 6 mm, (ii) a height (h) of less than 15 mm, for example from 5 mm to 13 mm, and (iii) a length (l) of less than 80 mm, for example from 20 mm to 40 mm or about 35 mm. In certain embodiments, the size of the implantable device 300 includes a width (w) of less than 24 mm, a height (h) of less than 15 mm, and a length (l) of less than 80 mm. In some embodiments, the size of the lossy housing 320 includes: (i) a width (w') of less than 24 mm, for example from 10 mm to 20 mm, (ii) a height (h') of less than 10 mm, for example from 5 mm to 9 mm, and (iii) a length (l') of less than 80 mm, for example from 20 mm to 40 mm. In certain embodiments, the size of the lossy housing 320 includes a width (w') of less than 24 mm, a height (h') of less than 10 mm, and a length (l') of less than 80 mm. In some embodiments, the size constraint 315 of the delivery mechanism 310 includes: (i) a width (w") of less than 30 mm, for example from 10 mm to 20 mm, (ii) a height (h") of less than 30 mm, for example from 10 mm to 20 mm, and (iii) a length (l") of less than 250 mm, for example from 40 mm to 100 mm. In certain embodiments, the size constraint 310 includes a width of less than 30 mm, a height of less than 30 mm, and a length of less than 250 mm.

In various embodiments, the delivery mechanism 320 is a laparoscopic port. A laparoscopic port for a minimally invasive procedure such as implantation of the device 300 may be exemplified as a cannula device or a trocar. Trocars typically comprise an outer housing and seal assembly, a sleeve with a lumen that fits inside the housing and seal assembly and a piercing stylus (e.g., an obturator) which slots into the lumen such that the tip of the stylus protrudes from the lower end of the device. The stylus may be used to create an opening in the abdominal wall through which the sleeve is inserted and fixed into place, following which the stylus is removed through an opening in the upper end of the device to allow insertion of a laparoscope or other surgical tools, or the device 300 in accordance with various aspects disclosed herein, through the lumen. A wide range of laparoscopic cannula devices and trocars exist having a variety of lengths and diameters. In some embodiments, the sleeve of the delivery mechanism 320 defines the size constraint 315 (e.g., the area of the lumen) of the delivery mechanism 320. In some embodiments, the size constraint 315 has a circular cross-section A-A, as shown in FIG. 3C. In certain embodiments, the size constraint 315 comprises a diameter (d) (width (w")=height (h")) of less than 30 mm, for example from 10 mm to 20 mm.

Figure 3D:
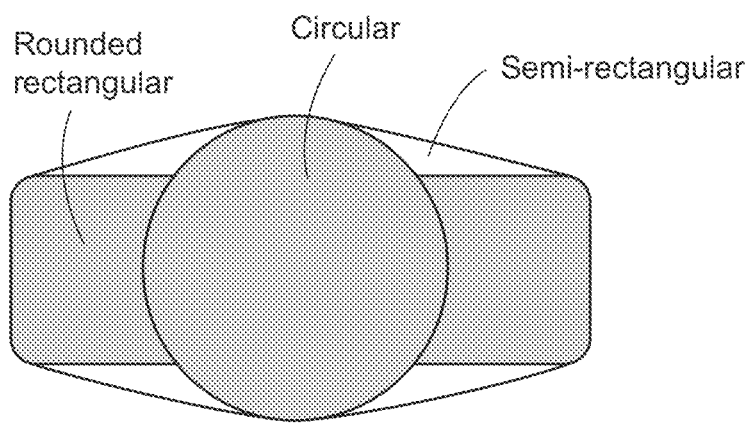
Figure 3E:
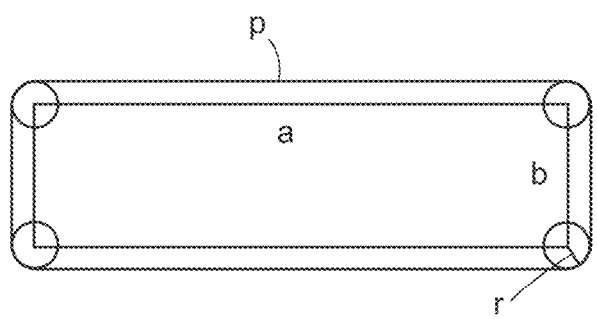
Figure 3F:
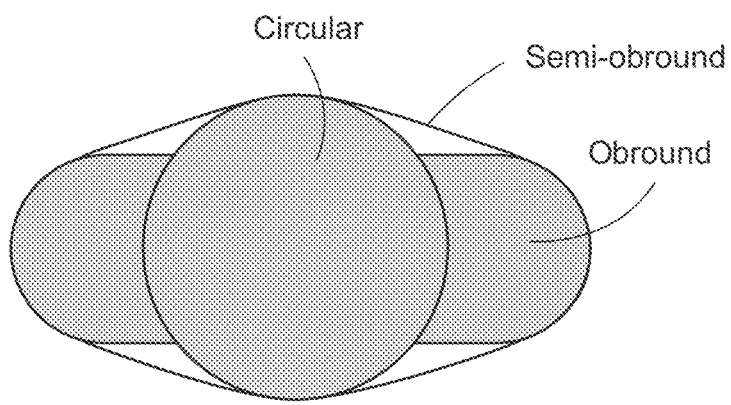

While the circular cross-section of the size constraint 315 is described herein in particular detail with respect to several described embodiments, it should be understood that other shapes or cross-sections of the size constraint 315 have been contemplated without departing from the spirit and scope of the present invention. For example, the size constraint 315 may have an oval, rounded rectangle, semi-rectangular, obround, or semi obround shape or cross-section. As used herein, the term "semi-rectangular" or "semi-rectangular cross section" means a rounded rectangular portion overlaid onto a larger central circular portion, as shown in FIG. 3D. As used herein, the term "rounded rectangle" or "rounded rectangular portion" means a shape obtained by taking the convex surface of four equal circles of radius r and placing their centers at the four corners of a rectangle with side lengths a and b and creating a perimeter p around the surface of the four equal circles and the rectangle, where the perimeter p of the shape is equal to $2(a+b+\pi r)$, as shown in FIG. 3E. As used herein, the term "semi-obround" or "semi-obround cross section" means an obround portion overlaid onto a larger central circular portion, as shown in FIG. 3F.

As shown in FIG. 3C, the receiving conductor structure 305 has area 335 defined by (ww)×(hh)×(ll). In some embodiments, the area 335 of the receiving conductor structure 305 is determined based on: (i) the size constraint 315 of the delivery mechanism 320, (ii) the size of the lossy housing 325, and (iii) the coupling factor between the receiving conductor structure 305 and the transmitting conductor structure of greater than 0.5. In some embodiments, the width (ww) is determined based on: (i) the width (w") or the diameter (d) of the size constraint 315. In some embodiments, the length (ll) is determined based on: (i) a length (l") of the size constraint 315. In some embodiments, the height (hh) is determined based on: (i) the height (h") or the diameter (d) of the size constraint 315, (ii) the height (h") of the lossy housing, and (iii) the predetermined distance (s). In order to increase the maximum possible area 340 of the receiving conductor structure 305 to maintain the coupling factor between the receiving conductor structure 305 and the transmitting conductor structure of greater than 0.5 while also accommodating for the predetermined distance (s), the height (hh) of the receiving conductor structure 305 may be adjusted in a vertical direction, the width (ww) of the receiving conductor structure 305 may be adjusted in a horizontally direction, and the (ll) may also be adjusted in a horizontally direction.

Figure 4A:
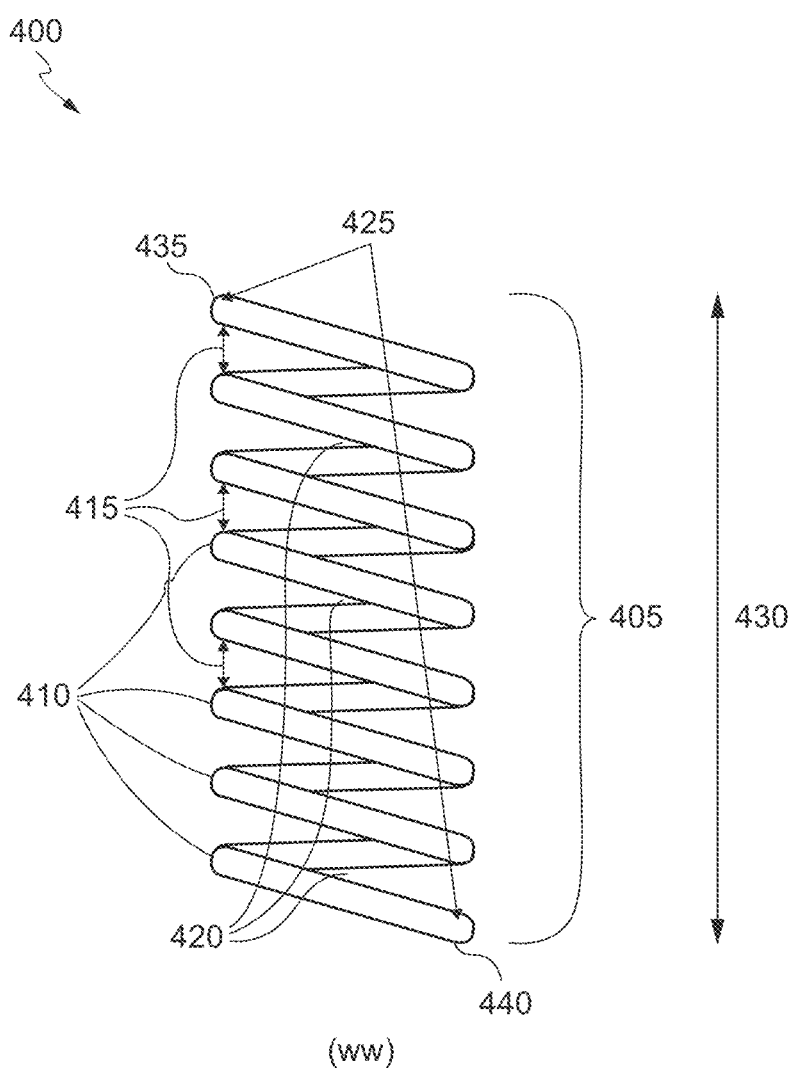
FIGS. 4A-4F show a wireless power receiver coil with a three-dimensional structure in accordance with various embodiments.
Figure 4B:
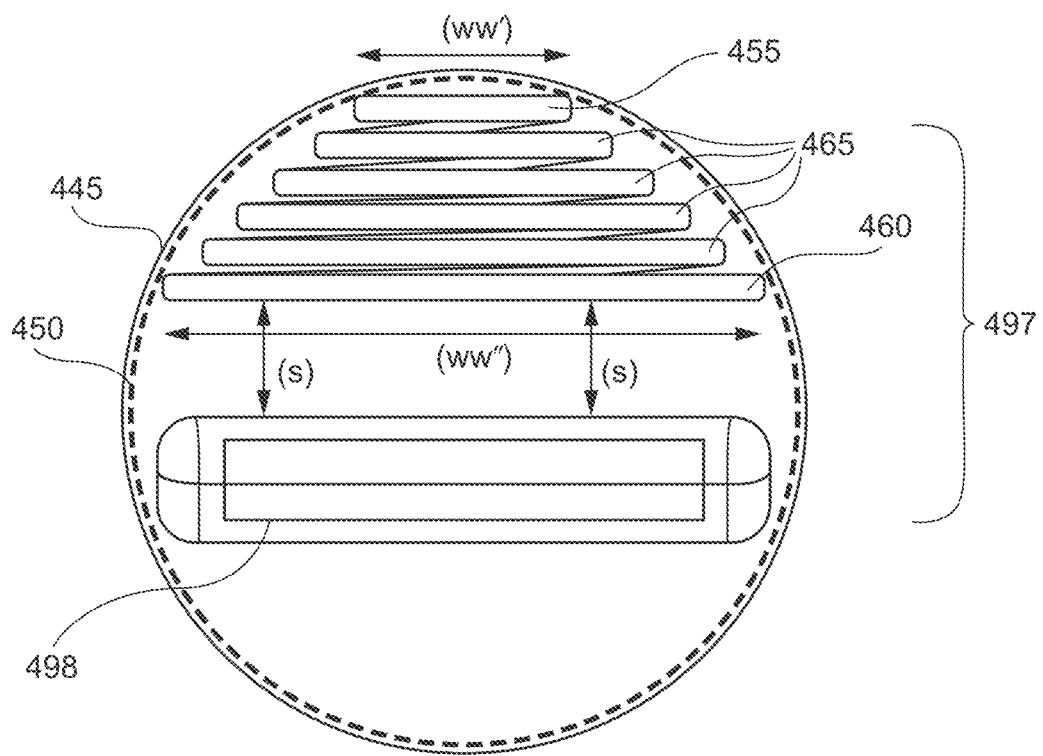
Figure 4C:
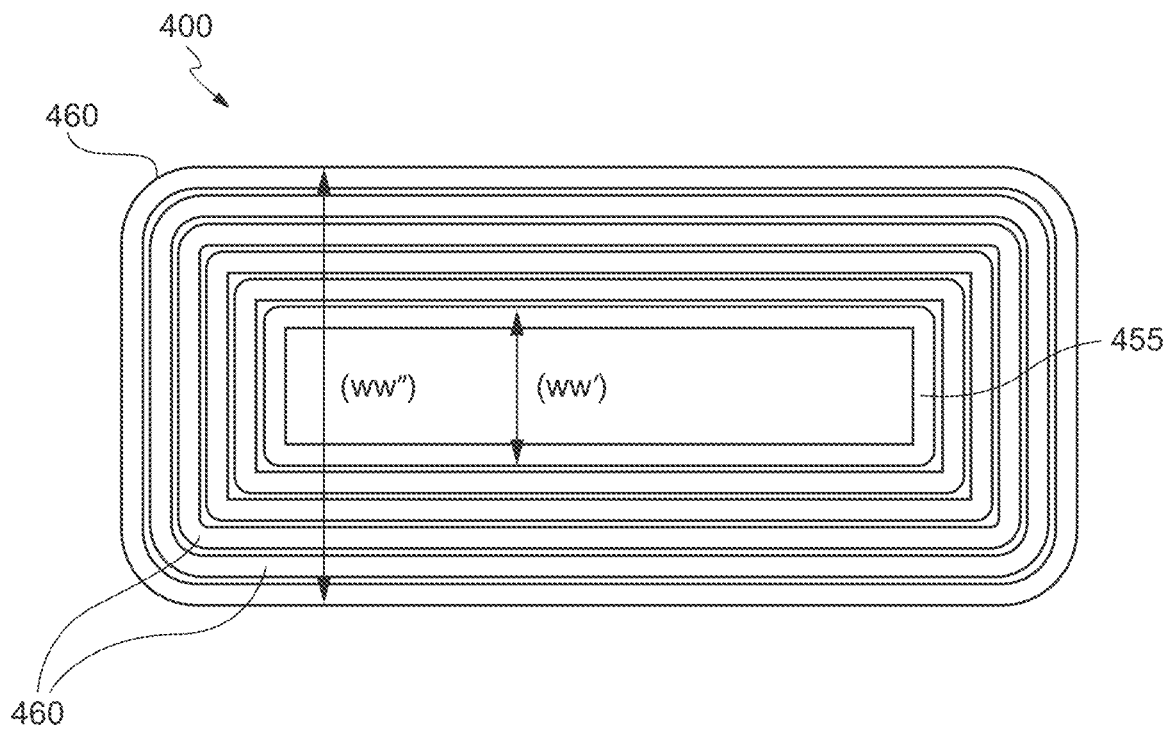
Figure 4D:
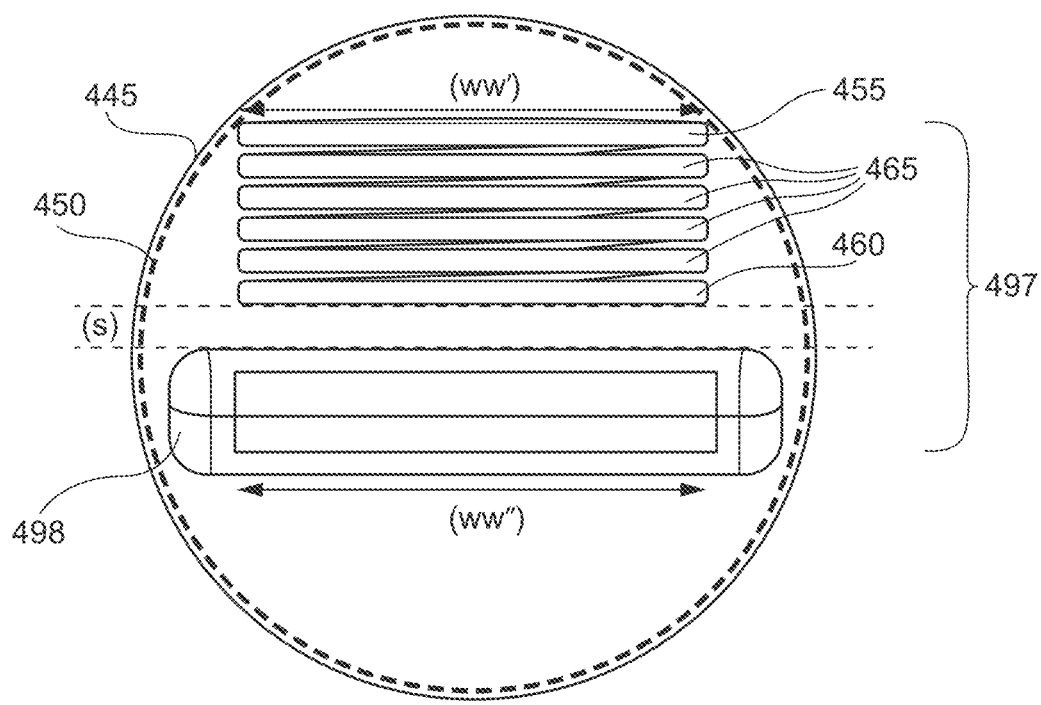
Figure 4E:
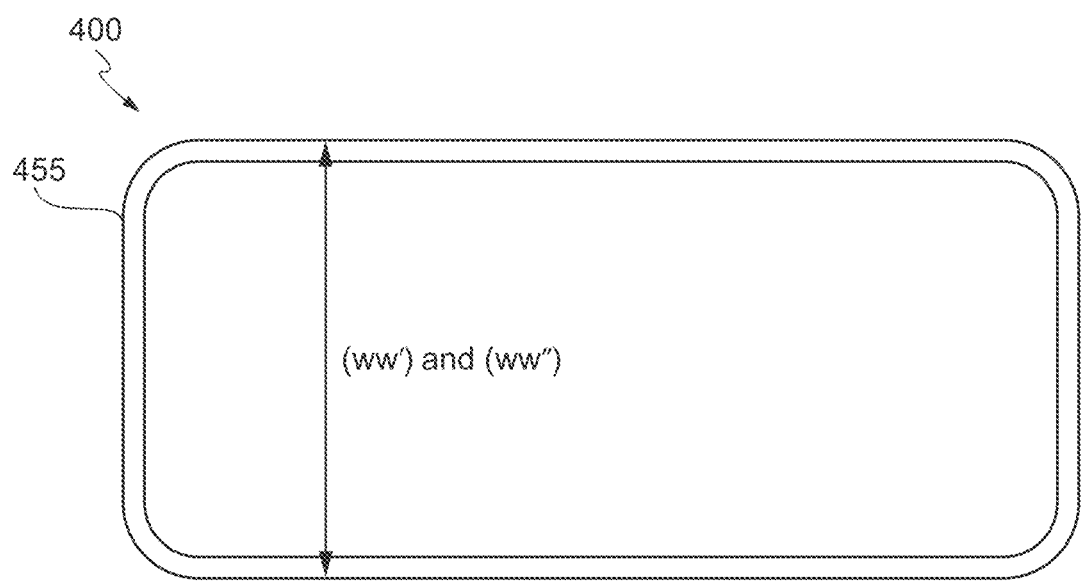

As shown in FIG. 4A, in order to increase the maximum possible area of the receiving conductor structure 400 (e.g., the receiving conductor structure 305 described with respect to FIGS. 3A, 3B, and 3C), the receiving conductor structure 400 may be formed in a three-dimensional manner rather than the conventional two-dimensional or planar coil. Testing has revealed that a three-dimensional coil is capable of maintaining sufficient coupling (i.e., the coupling factor between the receiving conductor structure 400 and the transmitting conductor structure of greater than 0.5) and power transfer with the transmitting conductor structure in such an enlarged area. In some embodiments, the receiving conductor structure 400 is a three-dimensional spiral or helix. The helix includes characteristics designed to maximize the area of the receiving conductor structure 400 in view of: (i) the size constraint of the delivery mechanism, (ii) the size of the lossy housing, and (iii) the coupling factor between the receiving conductor structure 400 and the transmitting conductor structure of greater than 0.5. In some embodiments, the characteristics of the helix include a shape 405, a number of turns 410, a pitch 415 (rise of the helix for one turn), a helix angle 420, a helix length 425 (a length of the coil), a total rise 430 of the helix (overall coil height (hh)), a width (ww), or combinations thereof.

In some embodiments, the shape 405 of the coil is rounded rectangular. However, it should be understood that other shapes of the coil have been contemplated without departing from the spirit and scope of the present invention. For example, the shape of the coil may be square, rectangular, circular, obround, etc. In some embodiments, the helix has greater than 2 turns or from 4 to 30 turns or from 4 to 15 turns, for example 9 turns, and a pitch between each of the turns from 10 μm to 1 cm or from 250 μm to 2 mm, for example about 500 μm. In some embodiments, the pitch between turns is the same or different. In some embodiments, the helix angle is from 5° to 85°, from 5° to 45°, or from 7° to 25°, for example, about 20°. In some embodiments, the helix length is from 2 cm to 100 cm or 25 cm to 75 cm, e.g., about 50 cm, from a first end 435 to a second end 440. In some embodiments, the total rise or overall coil height (hh) is less than 15 mm, for example from 5 mm to 13 mm.

As shown in FIGS. 4B, 4C, 4D, and 4E, a width (ww) of each of the turns 410 may be adjusted based on the position of the receiving conductor structure 400 in the delivery mechanism 445 and the size constraint 450 of the delivery mechanism 445. In various embodiments, a width (ww) of each of the turns 410 is less than or equal to a width of the lossy housing (e.g., the width (w") or the diameter (d) of the size constraint 315). In some embodiments, a width (ww') of the first turn 455 is less than a width (ww") of the last turn 460 in order to accommodate the curvature (i.e., the size constraint 450) of the delivery mechanism 445. In some embodiments, depending on the size constraint 450 of the delivery mechanism 445 and the predetermined distance (s), the turns 465 between the first turn 455 and the last turn 460 have a sequential increase in width (ww) from the first turn 455 such that a shape of the receiving conductor structure 400 is a pyramid (see, e.g., FIGS. 4B and 4C). In other embodiments, the width (ww') of the first turn 455 is the substantially the same as the width (ww") of the last turn 460 in order to accommodate the curvature (i.e., the size constraint 450) of the delivery mechanism 445. In some embodiments, depending on the size constraint 450 of the delivery mechanism 445 and the predetermined distance (s), the turns 465 between the first turn 455 and the last turn 460 have a same, smaller, or larger width (ww) from that of the first turn 455 or the last turn 460 such that a shape of the receiving conductor structure is configured to fit within the size constraint 450 of the delivery mechanism 445 (see, e.g., FIGS. 4D and 4E).

Figure 4F:
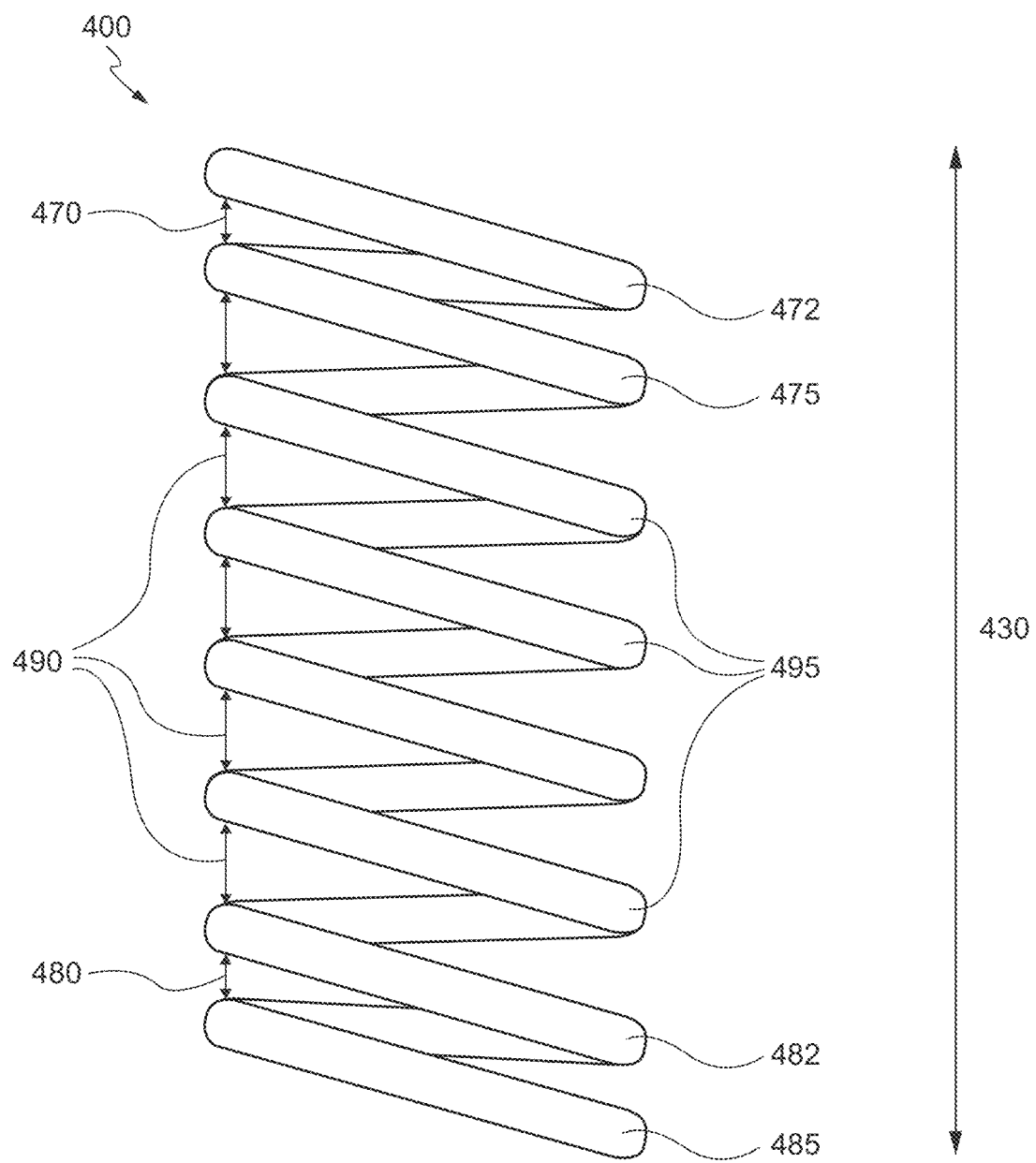

In various embodiments, the number of turns 410 and the helix length 425 are increased to maximize the area occupied by the receiving conductive structure 400. In some embodiments, the number of turns 410 and the helix length 425 are increased by adjusting the pitch 415, the helix angle 420, and the total rise 430. In some embodiments, as shown in FIG. 4F, the receiving conductor structure 400 is a helical structure with a total rise 430 or height that is determined based on: (i) a first pitch 470 between a first turn 472 and a second turn 475 of the receiving conductor structure 400; (ii) a second pitch 480 between a last turn 482 and a second to last turn 485 of the receiving conductor structure 400; and (iii) a third pitch 490 between remaining turns 495 between the second turn 475 and the second to last turn 485. The total rise 430 or height may be determined further based on the size constraint 450 of the delivery mechanism 445 and a size of the implantable device 497, in particular, the height of the implantable device 497. For example, the total rise 430 or height of the receiving conductor structure 400 may be determined to be less than the difference of the diameter or height of the delivery mechanism 445 and the height of the implantable device 497. In some embodiments, the first pitch 470 and the second pitch 480 are from 10 µm to 3 mm or from 250 µm to 2 mm, for example about 500 µm; and the third pitch 490 is from 500 µm to 1 cm or from 1 mm to 3 mm, for example about 2 mm. In some embodiments, the first pitch 470 and the second pitch 480 are less than the third pitch 490. In some embodiments, the first pitch 470 is the same as the second pitch 480. In other embodiments, the first pitch 470 is different from the second pitch 480.

Accordingly, by adjusting the width (ww) of each turn 410 and increasing the total rise 430 or height of the receiving conductive structure 400 it is possible to increase the number of turns 410 and the helix length 425 to maximize the area occupied by the receiving conductive structure 400. The area occupied by the receiving conductive structure 400 is maximized while fitting the receiving conductive structure 400 within the sizing constraint 450 of the delivery mechanism 445 even with the predetermined distance (s) between the lossy housing 498 and the receiving conductive structure 400.

Figure 5A:
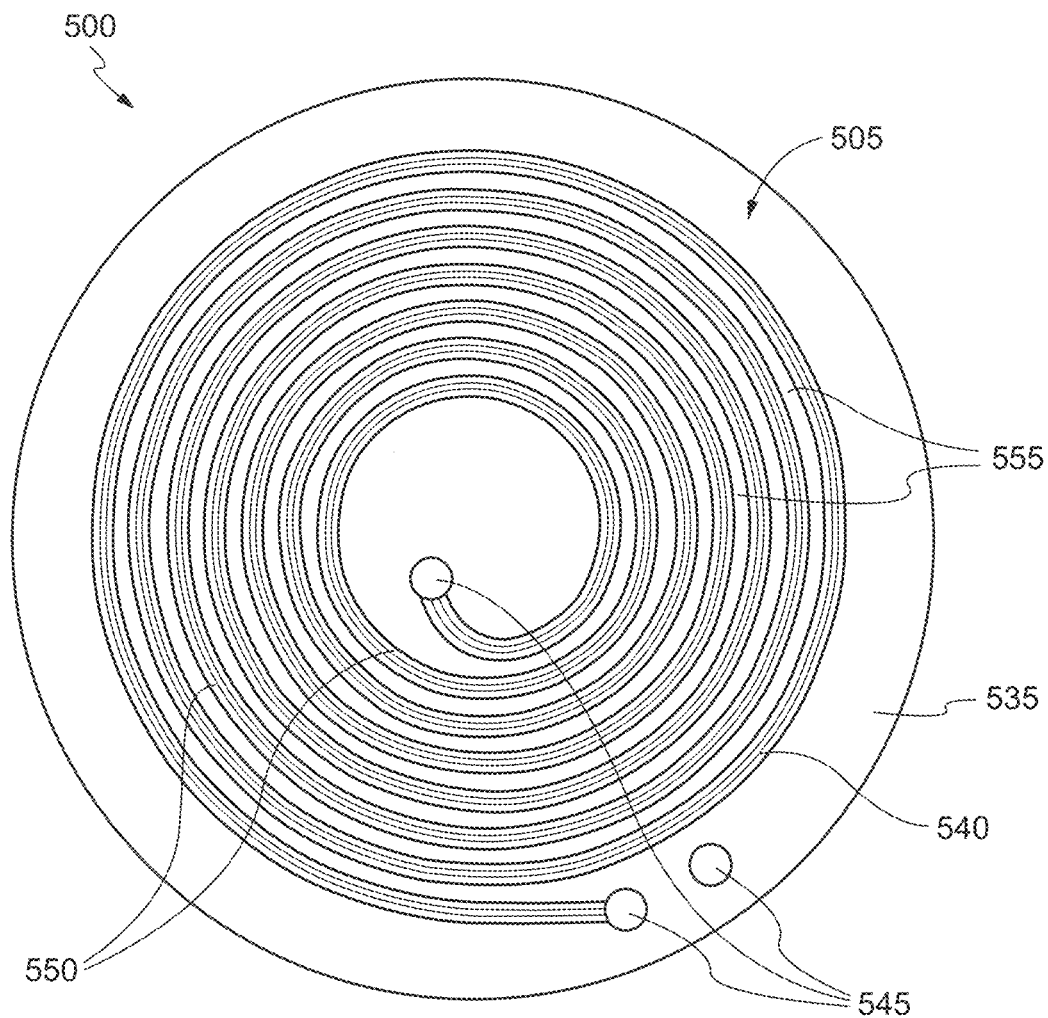
Figure 5B:
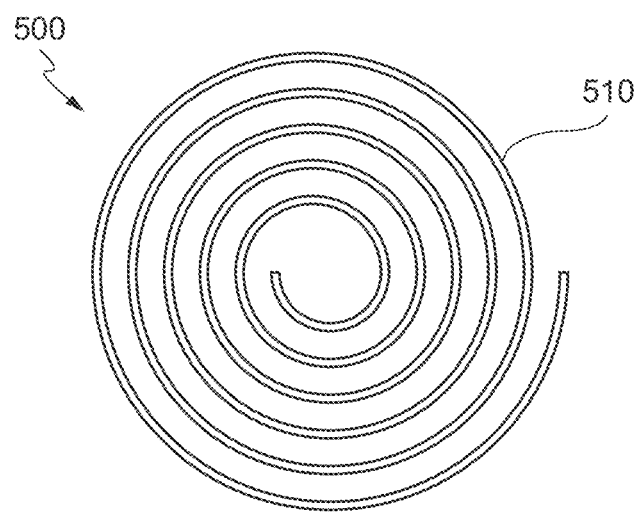
Figure 5C:
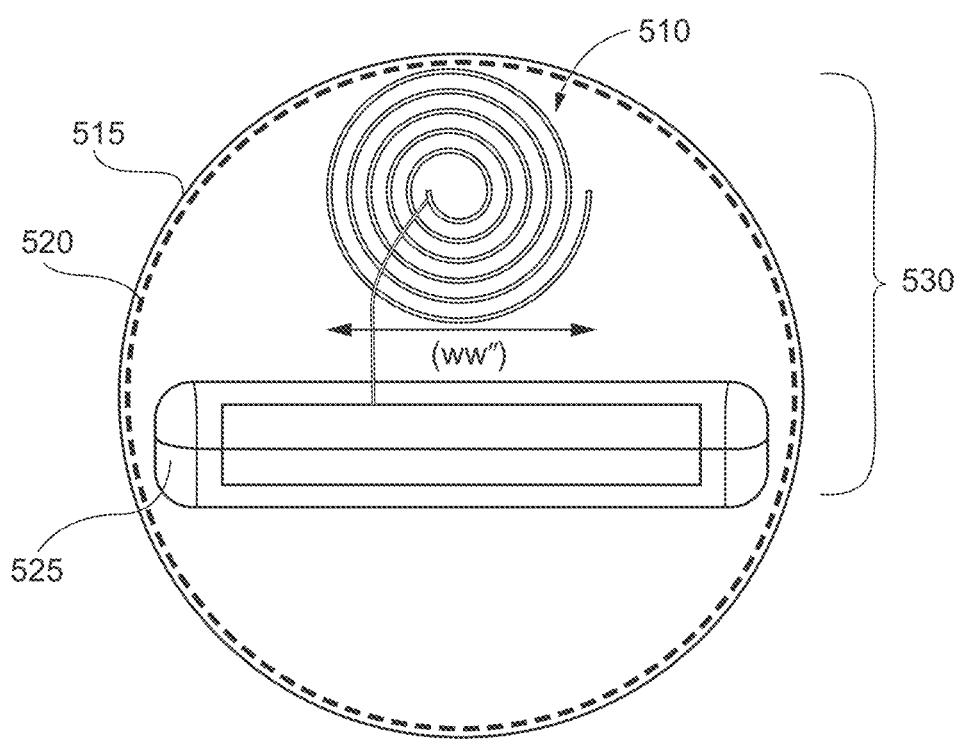
Figure 5D:
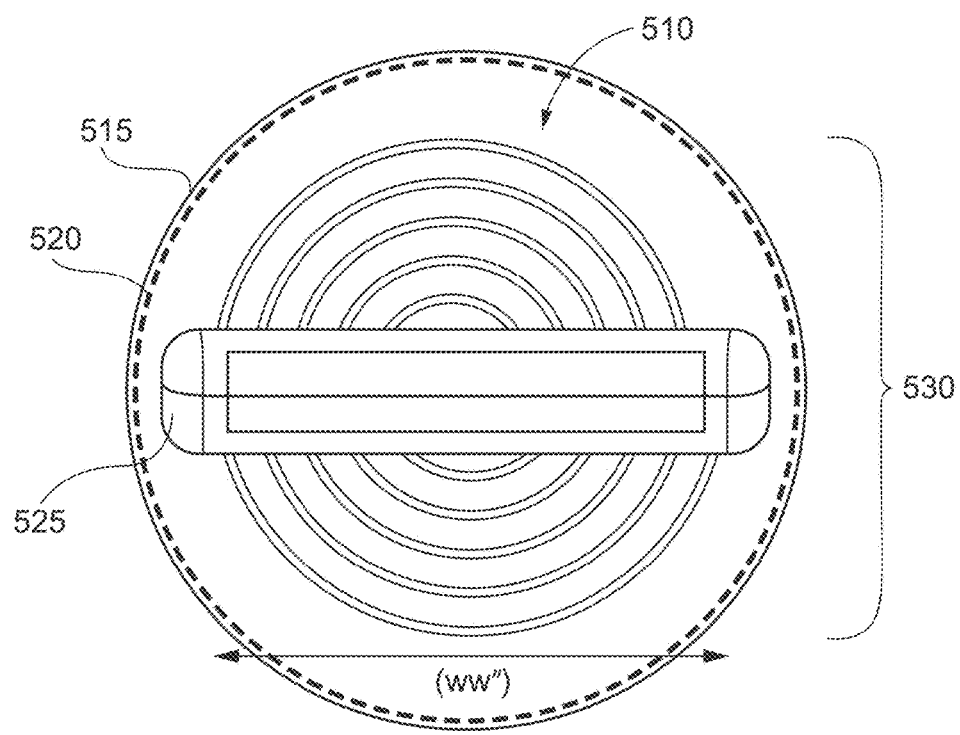
Figure 5E:
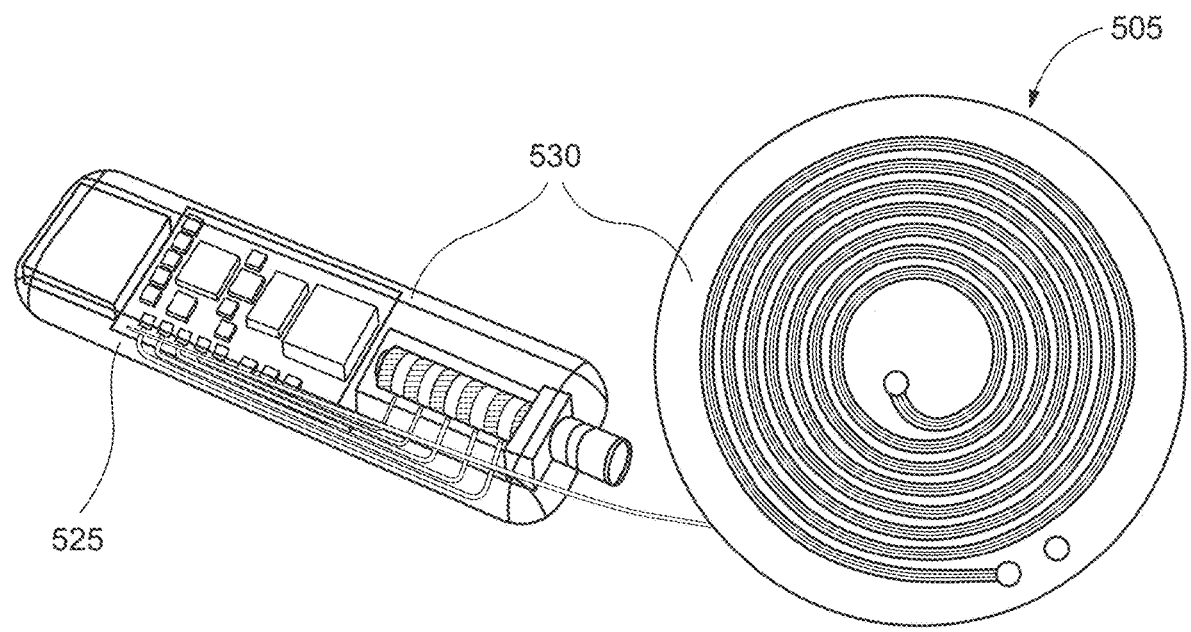

As shown in FIG. 5A, in order to increase the maximum possible area of the receiving conductor structure 500 (e.g., the receiving conductor structure 305 described with respect to FIGS. 3A, 3B, and 3C), the receiving conductor structure 500 may be formed as a two-dimensional or planar coil 505. As shown in FIG. 5B, the two-dimensional or planar coil 505 may be rolled up into a three-dimensional structure 510. In various embodiments, the two-dimensional or planar coil 505 is rolled up into a three-dimensional structure 510 that is capable of fitting within the delivery mechanism 515 in view of: (i) the size constraint 520 of the delivery mechanism 515 and (ii) the size of the lossy housing 525 (see, e.g., FIGS. 5C and 5D). In some embodiments, a size of the three-dimensional structure is determined based on: (i) a size constraint of the delivery mechanism 515 for the implantable device, (ii) a size of the lossy housing 525, (iii) an area of the receiving conductor structure, and (iv) a coupling factor between the receiving conductor structure and a transmitting conductor structure of greater than 0.5. By rolling up the two-dimensional or planar coil 505 into the three-dimensional structure 510 it is possible to deliver the two-dimensional or planar coil 505 via the delivery mechanism 515 to an implant site. As shown in FIG. 5E, once the implantable device 530 has been delivered to the implant site via the delivery mechanism 515, the three-dimensional structure 510 is capable of being unfurled back into the two-dimensional or planar coil 505. Testing has revealed that once the two-dimensional or planar coil is unfurled it is capable of maintaining sufficient coupling (i.e., the coupling factor between the receiving conductor structure 500 and the transmitting conductor structure of greater than 0.5) and power transfer with the transmitting conductor structure in such an enlarged area.

In various embodiments, the receiving conductor structure 500 comprises a substrate 535. In some embodiments, the substrate 535 is comprised of one or more layers of dielectric material (i.e., an insulator). The dielectric material may be selected from the group of electrically nonconductive materials consisting of organic or inorganic polymers, ceramics, glass, glass-ceramics, polyimide-epoxy, epoxy-fiberglass, and the like. In certain embodiments, the dielectric material is a polymer of imide monomers (i.e., a polyimide), a liquid crystal polymer (LCP) such as Kevlar®, parylene, polyether ether ketone (PEEK), or combinations thereof. In some embodiments, one or more conductive traces or wirings 540 are formed on a portion of the substrate 535. As used herein, the term "formed on" refers to a structure or feature that is formed on a surface of another structure or feature, a structure or feature that is formed within another structure or feature, or a structure or feature that is formed both on and within another structure or feature.

In various embodiments, the one or more conductive traces 540 are a plurality of traces, for example, two or more conductive traces or from two to twenty-four conductive traces. The plurality of conductive traces 540 are comprised of one or more layers of conductive material. The conductive material selected for the one or more conductive traces 550 should have good electrical conductivity and may include pure metals, metal alloys, combinations of metals and dielectrics, and the like. For example, the conductive material may be gold (Au), gold/chromium (Au/Cr), platinum (Pt), platinum/iridium (Pt/Ir), titanium (Ti), gold/titanium (Au/Ti), or any alloy thereof. The one or more conductive traces 540 may be deposited onto a surface of the substrate 535 by using thin film deposition techniques well known to those skilled in the art such as by sputter deposition, chemical vapor deposition, metal organic chemical vapor deposition, electroplating, electroless plating, and the like. In some embodiments, the thickness of the one or more conductive traces 540 is dependent on the particular inductance desired for receiving conductor structure 500, in order to enlarge the area of the receiving conductor structure 500. In certain embodiments, each of the one or more conductive traces 540 has a thickness from 0.5 µm to 100 µm or from 25 µm to 50 µm, for example about 25 µm or about 40 µm. In some embodiments, each of the one or more conductive traces 225 has a length (m) of about 5 cm to 200 cm or 50 cm to 150 cm, e.g., about 80 cm. In some embodiments, the conductive traces 540 are interconnected and connected to the implantable neurostimulator using one or more vias 545 or wiring layers formed within the substrate 535.

In various embodiments, the conductive traces 540 are formed with a predetermined shape to enlarge the area of the receiving conductor structure 500. For example, the receiving conductor structure 500 may comprise the one or more conductive traces or wirings 540 formed on the substrate 535 in a spiral shape. The spiral shape 545 may include characteristics designed to maximize the area of the receiving conductor structure 500 that can be fabricated on the substrate 535 and fit within the size constraint 520 of a delivery mechanism 515 while also taking into consideration a size of the lossy housing 525 of an implantable device 530. In some embodiments, the characteristics of the spiral shape include a predetermined number of turns 550 and a predetermined pitch 555 between each of the turns 525 to maximize the overall area obtainable for the receiving conductor structure 500. In certain embodiments, the spiral shape has 2 or more turns 550, for example from 2 to 25 turns, and a pitch 555 between each of the turns from 10 μm to 1 cm or from 250 μm to 2 mm, for example about 350 μm. Accordingly, the spiral shape can maximize the area of the receiving conductor structure 500 that can be fabricated from the substrate.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A medical device comprising:
   a lossy housing surrounding a power supply;
   a receiving coil configured to exchange power wirelessly via a wireless power transfer signal and deliver the power to the power supply, wherein the receiving coil is a helical structure comprising a plurality of turns having a sequential increase in width;
   a gap provided between the lossy housing and the receiving coil on a vertical plane; and
   a spacer that fills in at least a portion of the gap to maintain the lossy housing a predetermined distance from the receiving coil, wherein the spacer surrounds an entirety of the receiving coil.

2. The medical device of claim 1, wherein the spacer is silicone, a polymer dispersion, a chemical vapor deposited poly(p-xylylene) polymer, or a polyurethane.

3. The medical device of claim 1, wherein the spacer is attached to one or more surfaces of the receiving coil.

4. The medical device of claim 1, wherein the helical structure is three-dimensional and a total rise of the helical structure is determined based on a shape, a number of turns, a pitch of each turn, a helix length, a helix angle, or a combination thereof.

5. The medical device of claim 1, wherein a width of each of the plurality of turns is less than or equal to a width of the lossy housing.

6. The medical device of claim 1, wherein a width of a first turn of the plurality of turns is less than a width of a last turn of the plurality of turns.

7. A medical device comprising:
   a lossy housing;
   power supply within the lossy housing and connected to an electronics module;
   a receiving coil configured to exchange power wirelessly via a wireless power transfer signal and deliver the power to the power supply a gap provided between the lossy housing and the receiving coil; and
   a spacer that fills in at least a portion of the gap to maintain the lossy housing a predetermined distance from the receiving coil, wherein the spacer surrounds an entirety of the receiving coil,
   wherein the receiving coil is a helical structure comprising a first turn, a last turn, and one or more turns disposed between the first turn and the last turn; and
   wherein a width of the first turn is less than a width of the last turn, and wherein the one or more turns have a sequential increase in width from the first turn to the last turn.

8. The medical device of claim 7, wherein the receiving coil is aligned with the lossy housing on a vertical plane.

9. The medical device of claim 7, wherein the receiving coil comprises wound wire formed from conductive material, and the conductive material is comprised of gold (Au), gold/chromium (Au/Cr), platinum (Pt), platinum/iridium (Pt/Ir), titanium (Ti), gold/titanium (Au/Ti), or any alloy thereof.

10. A neuromodulation system comprising:
    a transmitting conductive structure configured to exchange power wirelessly via a wireless power transfer signal;
    an implantable neurostimulator including:
      a lossy housing;
      a connector attached to a hole in the lossy housing;
      one or more feedthroughs that pass through the connector;
      an electronics module within the lossy housing and connected to the one or more feedthroughs;
      a power supply within the lossy housing and connected to the electronics module;
      a receiving conductive structure disposed outside of the lossy housing and connected to the power supply, wherein the receiving conductive structure is configured to exchange power wirelessly with the transmitting conductive structure via the wireless power transfer signal and deliver the power to the power supply, and
    wherein the receiving conductive structure is a helical structure comprising a plurality of turns having a sequential increase in width,
      a gap provided between the lossy housing and the receiving conductive structure on a vertical plane; and
      a spacer that fills in at least a portion of the gap to maintain the lossy housing a predetermined distance from the receiving conductive structure, wherein the spacer surrounds an entirety of the receiving conductive structure, and
    a lead assembly including:
      a lead body including a conductor material;
      a lead connector that connects the conductor material to the one or more feedthroughs; and
      one or more electrodes connected to the conductor material.

11. The neuromodulation system of claim 10, wherein the spacer is silicone, a polymer dispersion, a chemical vapor deposited poly(p-xylylene) polymer, or a polyurethane.

12. The neuromodulation system of claim 10, wherein the spacer is attached to one or more surfaces of the receiving coil.

13. The neuromodulation system of claim 10, wherein the helical structure is three-dimensional and a total rise of the helical structure is determined based on a shape, a number of turns, a pitch of each turn, a helix length, a helix angle, or a combination thereof.

14. The neuromodulation system of claim 10, wherein a width of each turn of the plurality of turns is less than or equal to a width of the lossy housing.

15. The neuromodulation system of claim 10, wherein a width of a first turn of the plurality of turns is less than a width of a last turn of the plurality of turns.

* * * * *